US006803191B2

(12) United States Patent
Srikantha et al.

(10) Patent No.: US 6,803,191 B2
(45) Date of Patent: Oct. 12, 2004

(54) *CANDIDA ALBICANS* TWO-COMPONENT HYBRID KINASE GENE, CANIK1, AND USE THEREOF

(75) Inventors: Thyagarajan Srikantha, Coralville, IA (US); David R. Soll, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/424,951

(22) PCT Filed: Jun. 5, 1998

(86) PCT No.: PCT/US98/11658

§ 371 (c)(1),
(2), (4) Date: Jan. 20, 2000

(87) PCT Pub. No.: WO98/55654

PCT Pub. Date: Dec. 10, 1998

(65) Prior Publication Data

US 2002/0137034 A1 Sep. 26, 2002

Related U.S. Application Data

(60) Provisional application No. 60/048,914, filed on Jun. 6, 1997.

(51) Int. Cl.[7] .......................... C12Q 1/68; C07H 21/04

(52) U.S. Cl. ................... 435/6; 435/252.3; 435/254.22; 536/23.1; 536/24.1

(58) Field of Search ............................. 536/23.1, 24.1; 435/6, 252.3, 254.22

(56) References Cited

U.S. PATENT DOCUMENTS 5,939,306 A  *  8/1999  Alex et al. ............... 435/252.3

FOREIGN PATENT DOCUMENTS

WO    96/40939    12/1996

OTHER PUBLICATIONS

David R. Soll, "Gene regulation during high–frequency switching in *Candida albicans*" Microbiology, vol. 143, 1997, pp 279–288,XP002083237.
Database Swiss–Prot Accession No. p46588, Jun. 15, 1995 Ball T and Rosamond J: XP002083293 DNA Polymerase III gene (po13) from *Candida albicans*.
Nagahashi et al., Isolation of CaSLNI and CaNIK1, the genes for osmosensing histidine kinase homologues, from the pathogenic fungus *Candida albicans*: Microbiology, vol. 144, 1998, pp 425–432, XP002083238.
Srikantha et al., The WH11 gene of *Candida albicans* is regulated in two distinct developmental programs through the same transcription activation sequences: Journal Of Bacteriology, vol. 179, No. 12, 1997, pp 3837–3844, XP002083239.
Srikantha et al., "The sea pansy *Renilla reniformis* luciferas serves as a sensitive bioluminescent reporter, for differential gene expression in *Candida albicans*" Journal of Bacteriology, vol. 178, No. 1, 1996 pp 121–129, XP00208236.
Timerlake, W.E., "Cellular Reporters for Antifungal Drug Discovery", PAP Conference Discovery Mode Action Antifungal Agent, 1995, pp 17–29 XP000603570.

* cited by examiner

*Primary Examiner*—James Ketter
*Assistant Examiner*—David Lambertson
(74) *Attorney, Agent, or Firm*—Foley & Lardner, LLP

(57) ABSTRACT

A *Candida albicans* gene, CaNik1, is involved in phenotypic switching which is significant because of a direct correlation between the switching and the level of virulence of the organism. A method of screening for anti-fungal pharmaceutical candidates entails bringing a test substance into contact with cells containing a CaNik1 gene or a variant thereof and then monitoring the effect, if any, on the level of expression of the gene.

15 Claims, 10 Drawing Sheets

FIG. 1A

```
1531  Slb1⟶
GAGATTAGAACACCATTGAATGGGATTATTGGWATGACYCAGTTGTCRCTTGATACAGAG  1590
GluIleArgThrProLeuAsnGlyIleIleGlyMetThrGlnLeuSerLeuAspThrGlu   530
                    H1
TTGACRCAGTACCAACGAGAGATGTTGTCGATTGTGCATAACTTGGCAAATTCCTTGTTG  1650
LeuThrGlnTyrGlnArgGluMetLeuSerIleValHisAsnLeuAlaAsnSerLeuLeu   550

ACCATTATAGACGATATATTGGATATTTCTAAGATTGAGGCGAATAGAATGACGGTGGAA  1710
ThrIleIleAspAspIleLeuAspIleSerLysIleGluAlaAsnArgMetThrValGlu   570

CAGATTGATTTTTCATTAAGAGGGACAGTGTTTGGTGCATTGAAAACGTTAGCCGTCAAA  1770
GlnIleAspPheSerLeuArgGlyThrValPheGlyAlaLeuLysThrLeuAlaValLys   590

GCTATTGAAAAAACCTAGACTTGACCTATCAATGTGATTCATCGTTTCCAGATAATCTT  1830
AlaIleGluLysAsnLeuAspLeuThrTyrGlnCysAspSerSerPheProAspAsnLeu   610

ATTGGAGATAGTTTTAGATTACGACAAGTTATTCTTAACTTGGCTGGTAATGCTATTAAG  1890
IleGlyAspSerPheArgLeuArgGlnValIleLeuAsnLeuAlaGlyAsnAlaIleLys   630
                                  N
TTTACTAAAGAGGGGAAAGTTAGTGTTAGTGTGAAAAAGTCTGATAAAATGGTGTTAGAT  1950
PheThrLysGluGlyLysValSerValSerValLysLysSerAspLysMetValLeuAsp   650

AGTAAGTTGTTGTTAGAGGTTTGTGTTAGCGACACGGGAATAGGTATAGAGAAAGACAAA  2010
SerLysLeuLeuLeuGluValCysValSerAspThrGlyIleGlyIleGluLysAspLys   670
                               G1
TTGGGATTGATTTTCGATACCTTCTGTCAAGCTGATGGTTCTACTACAAGAAAGTTTGGT  2070
LeuGlyLeuIlePheAspThrPheCysGlnAlaAspGlySerThrThrArgLysPheGly   690
   ⟵Slb2
GGTACAGGTTTAGGGTTGTCAATTTCCAAACAGTTGATACATTTAATGGGTGGAGAGATA  2130
GlyThrGlyLeuGlyLeuSerIleSerLysGlnLeuIleHisLeuMetGlyGlyGluIle   710
     G2
TGGGTTACTTCGGAGTATGGATCCGGRTCAAACTTTTATTTTACGGTGTGCGTGTCGCCA  2190
TrpValThrSerGluTyrGlySerGlySerAsnPheTyrPheThrValCysValSerPro   730

TCTAATATTAGATATACTCGACAAACCGAACAATTGTTACCATTTAGTTCCCATTATGTG  2250
SerAsnIleArgTyrThrArgGlnThrGluGlnLeuLeuProPheSerSerHisTyrVal   750

TTATTTGTATCGACTGAGCATACTCAAGAAGAACTTGATGTGTTGAGAGATGGAATTATA  2310
LeuPheValSerThrGluHisThrGlnGluGluLeuAspValLeuArtAspGlyIleIle   770
```

FIG. 1B

```
GAACTTGGATTGATACCTATAATAGTGAGAAATATTGAAGATGCAACATTGACTGAGCCG 2370
GluLeuGlyLeuIleProIleIleValArgAsnIleGluAspAlaThrLeuThrGluPro   790

GTGAAATATGATATAATTATGATTGATTCGATAGAGATTGCCAAAAAGTTGAGGTTGTTA 2430
ValLysTyrAspIleIleMetIleAspSerIleGluIleAlaLysLysLeuArgLeuLeu   810

TCGGAGGTTAAATATATTCCGTTGGTTTTGGTCCATCATTCTATTCCACAGTTGAATATG 2490
SerGluValLysTyrIleProLeuValLeuValHisHisSerIleProGlnLeuAsnMet   830

AGAGTATGTATTGATTTGGGGATATCTTCCTATGCAAATACGCCATGTTCGATCACGGAC 2550
ArgValCysIleAspleuGlyIleSerSerTyrAlaAsnThrProCysSerIleThrAsp   850

TTGGCCAGTGCGATTATACCAGCGTTGGAGTCGAGATCTATATCACAGAACTCAGACGAG 2610
LeuAlaSerAlaIleIleProAlaLeuGluSerArgSerIleSerGlnAsnSerAspGlu   870

TCGGTGAGGTACAAAATATTACTAGCAGAGGACAACCTCGTCAATCAGAAACTTGCAGTT 2670
SerValArgTyrLysIleLeuLeuAlaGluAspAsnLeuValAsnGlnLysLeuAlaVal   890

AGGATATTAGAAAAGCAAGGGCATCTGGTGGAAGTAGTTGAGAACGGACTCGAGGCGTAC 2730
ArgIleLeuGluLysGlnGlyHisleuValGluValValGluAsnGlyLeuGluAlaTyr   910
                                                   ←──── S1b3
GAAGCGATTAAGAGGAATAAATATGATGTGGTGTTGATGGATGTGCAAATGCCT       2784
GluAlaIleLysArgAsnLysTyrAspValValLeuMetAspValGlnMetPro        928
                                        ─────────────
                                              D
```

FIG. 2A

```
ATGAACCCCACTAAAAAACCTCGGTTATCACCAATGCAGCCCTCTGTTTTTGAAATACTC  60
MetAsnProThrLysLysProArgLeuSerProMetGlnProSerValPheGluIleLeu  20

AACGACCCTGAGCTTTATAGTCAGCACTGTCATAGCCTTAGGGAAACACTTCTTGATCA   20
AsnAspProGluLeuTyrSerGlnHisCysHisSerLeuArgGluThrLeuLeuAspHis  40

TTCAACCATCAAGCTACACTTATCGACACTTATGAACATGAACTAGAAAAATCCAAAAAT 180
PheAsnHisGlnAlaThrLeuIleAspThrTyrGluHisGluLeu|Glu|LysSerLysAsn  60

GCCAACAAAGCGTCCCAACAAGCACTTAGTGAAATAGGTACAGTTGTTATATCTGTTGCC 240
AlaAsnLysAlaSerGlnGlnAlaLeuSerGluIleGlyThrValValIleSerValAla  80

ATGGGAGACTTGTCGAAAAAAGTTGAGATTCACACAGTAGAAAATGACCCTGAGATTTTA 300
MetGlyAspLeuSerLysLysValGluIleHisThrValGluAsnAspProGluIleLeu 100

AAAGTCAAAATCACCATCAACACCATGATGGATCAATTACAGACATTTGCTAATGAGGTT 360
LysValLysIleThrIleAsnThrMetMetAspGlnLeuGlnThrPheAlaAsnGluVal 120

ACAAAAGTCGCCACCGAAGTCGCAAATGGTGAACTAGGTGGACAAGCGAAAAATGATGGA 420
ThrLysValAlaThrGluValAlaAsnGlyGluLeuGlyGlyGlnAlaLysAsnAspGly 140

TCTGTTGGTATTTGGAGATCACTTACAGACAATGTTAATATTATGGCTCTTAATTTAACT 480
SerValGlyIle|Trp|ArgSerLeuThrAspAsnValAsnIleMetAlaLeuAsnLeuThr 160

AACCAAGTGCGAGAAATTGCTGATGTCACACGTGCTGTTGCCAAGGGGGACTTGTCACGT 540
AsnGlnValArgGluIleAlaAspValThrArgAlaValAlaLysGlyAspLeuSerArg 180

AAAATTAATGTACACGCCCAGGGTGAAATCCTTCAACTTCAACGTACAATAAACACCATG 600
LysIleAsnValHisAlaGlnGlyGluIleLeuGlnGeuGlnArgThrIleAsnThrMet 200

GTGGATCAGTTACGAACGTTTGCATTCGAAGTATCTAAAGTTGCTAGAGATGTTGGTGTG 660
ValAspGlnLeuArgThrPheAlaPheGluValSerLysValAlaArgAspValGlyVal 220

CTTGGTATATTAGGAGGACAAGCGTTGATTGAAAATGTTGAAGGTATTTGGGAAGAGTTG 720
LeuGlyIleLeuGlyGlyGlnAlaLeuIleGluAsnValGluGlyIle|Trp|GluGluLeu 240

ACTGATAATGTCAATGCCATGGCTCTTAATTTGACTACACAAGTGAGAAATATTGCCAAT 780
ThrAspAsnValAsnAlaMetAlaLeuAsnLeuThrThrGlnValArgAsnIleAlaAsn 260
```

FIG. 2B

```
GTCACCACTGCCGTTGCCAAGGGGGATTTGTCGAAAAAAGTCACTGCTGATTGTAAGGGA  840
ValThrThrAlaValAlaLysGlyAspLeuSerLysLysValThrAlaAspCysLycGly   280

GAAATYCTTGATTTGAAACTTACTATTAATCAAATGGTGGACCGATTACAGAATTTTGCT  900
GluIleLeuAspLeuLysLeuThrIleAsnGlnMetValAspArgLeuGlnAsnPheAla   300

CTTGCGGTGACGACATTGTCGAGAGAGGTTGGTACTTTGGGTATTTTGGGTGGACAAGCT  960
LeuAlaValThrThrLeuSerArgGluValGlyThrLeuGlyIleLeuGlyGlyGlnAla   320

AACGTACAGGATGTTGAAGGTGCTTGGAAACAGGTTACAGAAAATGTCAACCTAATGGCT 1020
AsnValGlnAspValGluGlyAla[Trp]LysGlnValThrGluAsnValAsnLeuMetAla  340

ACTAATTTAACTAACCAAGTGAGATCTATTGCTACAGTTACTACTGCAGTTGCGCATGGT 1080
ThrAsnLeuThrAsnGlnValArgSerIleAlaThrValThrThrAlaValAlaHisGly   360

GATTTGTCGCAAAAGATTGATGGTCATCCCAAAGGAGAGATTTTACAATTGAAAAATACA 1140
AspLeuSerGlnLysIleAspGlyHisProLysGlyGluIleLeuGlnLeuLysAsnThr   380

ATCAACAAGATGGTGGACTCTTTGCAGTTGTTTGCATCAGAAGTGTCGAAAGTGGCACAA 1200
IleAsnLysMetValAspSerLeuGlnLeuPheAlaSerGluValSerLysValAlaGln   400

GATGTTGGTATTAATGGAAAATTAGGTATTCAAGCACAAGTTAGTGATGTTGATGGATTA 1260
AspValGlyIleAsnGlyLysLeuGlyIleGlnAlaGlnValSerAspValAspGlyLeu   420

TGGAAGGAGATTACGTCTAATGTAAATACCATGGCTTCAAATTTAACTTCGCAAGTGAGA 1320
[Trp]LysGluIleThrSerAsnValAsnThrMetAlaSerAsnLeuThrSerGlnValArg   440

GCTTTTGCACAGATTACTGCTGCTGCTACTGATGGGGATTTCACTAGATTTATTACTGTT 1380
AlaPheAlaGlnIleThrAlaAlaAlaThrAspGlyAspPheThrArgPheIleThrVal   460

GAAGCACTGGGAGAGATGGATGCGTTGAAAACAAAGATTAATCAAATGGTGTTTAACTTA 1440
GluAlaLeuGlyGluMetAspAlaLeuLysThrLysIleAsnGlnMetValPheAsnLeu   480

AGGGAATCGCTTCAAAGGAATACTGCGGCTAGAGAAGCTGCTGAGTTGGCCAATAGTGCG 1500
ArgGluSerLeuGlnArgAsnThrAlaAlaArgGluAlaAlaGluLeuAlaAsnSerAla   500

AAATCCGAGTTTTTAGCAAACATGTCGCATGAGATTAGAACACCATTGAATGGGATTATT 1560
LysSerGluPheLeuAlaAsnMetSerHisGluIleArgThrProLeuAsnGlyIleIle   520
                                     H1
```

FIG. 2C

```
GGWATGACYCAGTTGTCRCTTGATACAGAGTTGACRCAGTACCAACGAGAGATGTTGTCG 1620
GlyMetThrGlnLeuSerLeuAspThrGluLeuThrGlnTyrGlnArgGluMetLeuSer  540

ATTGTGCATAACTTGGCAAATTCCTTGTTGACCATTATAGACGATATATTGGATATTTCT 1680
IleValHisAsnLeuAlaAsnSerLeuLeuThrIleIleAspAspIleLeuAspIleSer  560

AAGATTGAGGCGAATAGAATGACGGTGGAACAGATTGATTTTTCATTAAGAGGGACAGTG 1740
LysIleGluAlaAsnArgMetThrValGluGlnIleAspPheSerLeuArgGlyThrVal  580

TTTGGTGCATTGAAAACGTTAGCCGTCAAAGCTATTGAAAAAAACCTAGACTTGACCTAT 1800
PheGlyAlaLeuLysThrLeuAlaValLysAlaIleGluLysAsnLeuAspLeuThrTyr  600

CAATGTGATTCATCGTTTCCAGATAATCTTATTGGAGATAGTTTTAGATTACGACAAGTT 1860
GlnCysAspSerSerPheProAspAsnLeuIleGlyAspSerPheArgLeuArgGlnVal  620

ATTCTTAACTTGGCTGGTAATGCTATTAAGTTTACTAAAGAGGGGAAAGTTAGTGTTAGT 1920
IleLeuAsnLeuAlaGlyAsnAlaIleLysPheThrLysGluGlyLysValSerValSer  640
          N
GTGAAAAAGTCTGATAAAATGGTGTTAGATAGTAAGTTGTTGTTAGAGGTTTGTGTTAGC 1980
ValLysLysSerAspLysMetValLeuAspSerLysLeuLeuLeuGluValCysValSer  660

GACACGGGAATAGGTATAGAGAAAGACAAATTGGGATTGATTTTCGATACCTTCTGTCAA 2040
AspThrGlyIleGlyIleGluLysAspLysLeuGlyLeuIlePheAspThrPheCysGln  680
   G1
GCTGATGGTTCTACTACAAGAAAGTTTGGTGGTACAGGTTTAGGGTTGTCAATTTCCAAA 2100
AlaAspGlySerThrThrArgLysPheGlyGlyThrGlyLeuGlyLeuSerIleSerLys  700
                            G2
CAGTTGATACATTTAATGGGTGGAGAGATATGGGTTACTTCGGAGTATGGATCCGGRTCA 2160
GlnLeuIleHisLeuMetGlyGlyGluIleTrpValThrSerGluTyrGlySerGlySer  720

AACTTTTATTTTACGGTGTGCGTGTCGCCATCTAATATTAGATATACTCGACAAACCGAA 2220
AsnPheTyrPheThrValCysValSerproSerAsnIleArgTyrThrArgGlnThrGlu  740

CAATTGTTACCATTTAGTTCCCATTATGTGTTATTTGTATCGACTGAGCATACTCAAGAA 2280
GlnLeuLeuProPheSerSerHisTyrValLeuPheValSerThrGluHisThrGlnGlu  760

GAACTTGATGTGTTGAGAGATGGAATTATAGAACTTGGATTGATACCTATAATAGTGAGA 2340
GluLeuAspValLeuArgAspGlyIleIleGluLeuGlyLeuIleProIleIleValArg  780
```

FIG. 2D

```
AATATTGAAGATGCAACATTGACTGAGCCGGTGAAATATGATATAATTATGATTGATTCG  2400
AsnIleGluAspAlaThrLeuThrGluProValLysTyrAspIleIleMetIleAspSer   800

ATAGAGATTGCCAAAAAGTTGAGGTTGTTATCGGAGGTTAAATATATTCCGTTGGTTTTG  2460
IleGluIleAlaLysLysLeuArgLeuLeuSerGluValLysTyrIleProLeuValLeu   820

GTCCATCATTCTATTCCACAGTTGAATATGAGAGTATGTATTGATTTGGGGATATCTTCC  2520
ValHisHisSerIleProGlnLeuAsnMetArgValCysIleAspLeuGlyIleSerSer   840

TATGCAAATACGCCATGTTCGATCACGGACTTGGCCAGTGCGATTATACCAGCGTTGGAG  2580
TyrAlaAsnThrProCysSerIleThrAspLeuAlaSerAlaIleIleProAlaLeuGlu   860

TCGAGATCTATATCACAGAACTCAGACGAGTCGGTGAGGTACAAAATATTACTAGCAGAG  2640
SerArgSerIleSerGlnAsnSerAspGluSerValArgTyrLysIleLeuLeuAlaGlu   880

GACAACCTCGTCAATCAGAAACTTGCAGTTAGGATATTAGAAAAGCAAGGGCATCTGGTG  2700
AspAsnLeuValAsnGlnLysLeuAlaValArgIleLeuGluLysGlnGlyHisLeuVal   900

GAAGTAGTTGAGAACGGACTCGAGGCGTACGAAGCGATTAAGAGGAATAAATATGATGTG  2760
GluValValGluAsnGlyLeuGluAlaTyrGluAlaIleLysArgAsnLysTyrAspVal   920

GTGTTGATGGATGTGCAAATGCCTGTAATGGGTGGGTTTGAAGCTACGGAGAAGATTCGA  2820
ValLeuMetAspValGlnMetProValMetGlyGlyPheGluAlaThrGluLysIleArg   940
         D

CAATGGGAGAAAAAGTCTAACCCAATTGACTCGTTGACCTTTAGGACTCCAATTATTGCC  2880
GlnTrpGluLysLysSerAsnProIleAspSerLeuThrPheArgThrProIleIleAla   960

CTCACTGCACACGCCATGTTAGGTGATAGAGAAAAGTCATTGGCCAAGGGGATGGACGAT  2940
LeuThrAlaHisAlaMetLeuGlyAspArgGluLysSerLeuAlaLysGlyMetAspAsp   980

TATGTGAGTAAGCCATTGAAGCCGAAATTGTTAATGCAGACGATAAAGAAGTGTATTCAT  3000
TyrValSerLysProLeuLysProLysLeuLeuMetGlnThrIleAsnLysCysIleHis  1000
                                                          H2
AATATTAACCAGTTGAAAGAATTGTCGAGAAATAGTAGGGGTAGCGATTTTGCAAAGAAG  3060
AsnIleAsnGlnLeuLysGluLeuSerArgAsnSerArgGlySerAspPheAlaLysLys  1020

ATGACCCGAAACACACCCGGCCGCACGACCCGTCAGGGGAGTGATGAGGGGAGTGTAAAG  3120
MetThrArgAsnThrProGlySerThrThrArgGlnGlySerAspGluGlySerValLys  1040
```

FIG. 2E

```
GACATGATTGGGGACACTCCCCGTCAAGGGAGTGTGGAGGGAGGGGGTACAAGTAGTAGA 3180
AspMetIleGlyAspThrProArgGlnGlySerValGluGlyGlyGlyThrSerSerArg 1060

CCAGTACAGAGAAGGTCTGCCAGGGAGGGGTCGATCACTACAATTAGTGAACAAATCGAC 3240
ProValGlnArgArgSerAlaArgGluGlySerIleThrThrIleSerGluGlnIleAsp 1080

CGTTAG                                                       3246
Arg***                                                       1082
```

CANDIDA ALBICANS TWO-COMPONENT HYBRID KINASE GENE, CANIK1, AND USE THEREOF

This application claims benefit of provisional application 60/048,914 filed Jun. 6, 1997.

This application describes microorganisms that have been deposited, in accordance with the Budapest Treaty, under ATCC Patent Deposit Designation: PTA-4456, with the following Deposit Identification Reference: Bacteriophage lambda EMBL3: Ca lambda 15.1.

BACKGROUND OF THE INVENTION

Candida is an opportunistic yeast that lives in the mouth, throat, intestines, and genitourinary tract of most humans. In a healthy human body, the population of Candida is kept in check by the immune system and by a competitive balance with other microorganisms. But when the body's immune system is compromised, as in AIDS patients and in patients undergoing immunosuppressive therapy, Candida will grow uncontrolled, leading to systemic infection called "Candida mycosis." If left untreated, such systemic infections frequently lead to the death of the patients.

Candida albicans is a species of particular interest to scientists and doctors because 90% of all cases of Candida mycosis are caused by this species.

At present, the therapy principally available for invasive infections is based on relatively few antimycotics, such as amphotericin B and flucytosine, or the azole derivatives fluconazole and itraconazole. These antimycotics cause serious side effects, such as renal insufficiency, hypocalcaemia and anaemia, as well as unpleasant constitutional symptoms such as fever, shivering and low blood pressure. Amphotericin B is toxic to the kidneys, for example, and yet the pharmaceutical is therapeutic only if administered at dose levels near to being toxic. A discussion of the pharmaceuticals used for treatment and their corresponding side effects can be found, for example, in Boyd, et al., BASIC MEDICAL MICROBIOLOGY (2d ed.), Little, Brown and Company, (1981).

Given the deficiencies of conventional therapies against Candida, a need exists for developing pharmaceuticals that are effective in this regard and also safe to use. One step in the development of such pharmaceuticals requires a method for screening compounds in order to identify pharmaceutical candidates.

SUMMARY OF THE INVENTION

It therefore is an object of the present invention to provide an isolated polynucleotide sequence coding for a protein that is linked to phenotypic switching in Candida albicans.

It is a further object of the invention to provide a method for screening compounds to identify pharmaceutical candidates for effectively inhibiting the pathogenicity of C. albicans.

In accomplishing these and other objects, there has been provided, according to one aspect of the present invention, an isolated polynucleotide that codes for such a protein and that hybridizes, under stringent conditions, to the polynucleotide sequence of SEQ ID NO:1, shown below in FIG. 1. In a preferred embodiment, the polynucleotide has the sequence of SEQ ID NO:3 (FIG. 2). In another preferred embodiment, the protein displays a kinase activity.

In accordance with another aspect of the present invention, a method is provided for screening compounds to identify pharmaceutical candidates. The inventive method comprises the steps of (A) providing a plurality of cells from yeast species that exhibit phenotypic switching, at least some of which contain (i) a polynucleotide coding for a CaNIK1 protein and (ii) a promoter that is operably linked to the polynucleotide, such that the plurality of cells produces the protein; then (B) bringing the plurality into contact with a test substance; and (C) assessing what effect, if any, the test substance has on the expression of the DNA segment. Assessment step (C) can comprise, for example, of monitoring the level either of the protein or the corresponding mRNA transcript produced by the plurality of cells. In another embodiment, step (C) comprises monitoring the level of kinase activity, within the plurality, that typifies the protein.

In yet another embodiment of the present invention, a promoter is operably linked to a reporter gene. In this context, step (C) comprises monitoring the level of transcription of the reporter gene, after contact between the plurality of cells and the test substance.

Other objects, features and advantages of the present invention will become apparent from the following detailed description. It should be understood, however, that the detailed description and the specific examples, only indicate preferred embodiments of the invention.

BRIEF DESCRIPTION OF THE DRAWINGS

FIGS. 1A–B show the nucleotide sequence (SEQ ID NO:11) (top row) of the PCR product encoding the region spanning the H1 and D domains and the deduced amino acid sequence of the CaNIK1 protein (SEQ ID NO:2) (bottom row). The amino acid residues of functional domains are underlined. The three degenerate primers used to isolate the PCR products are shown as Slb1, Slb2, and Slb3.

FIGS. 2A–E show the nucleotide sequence(SEQ ID NO:3) (top row) of the gene CaNik1 and the deduced primary amino acid sequence of the CaNIK1 protein(SEQ ID NO:11) (bottom row). The beginning of each unique repeat is represented within the rectangle. The potential amino acid residues of different functional domains are underlined.

FIG. 4 provides a description of λSA15.1.

Figure 3:
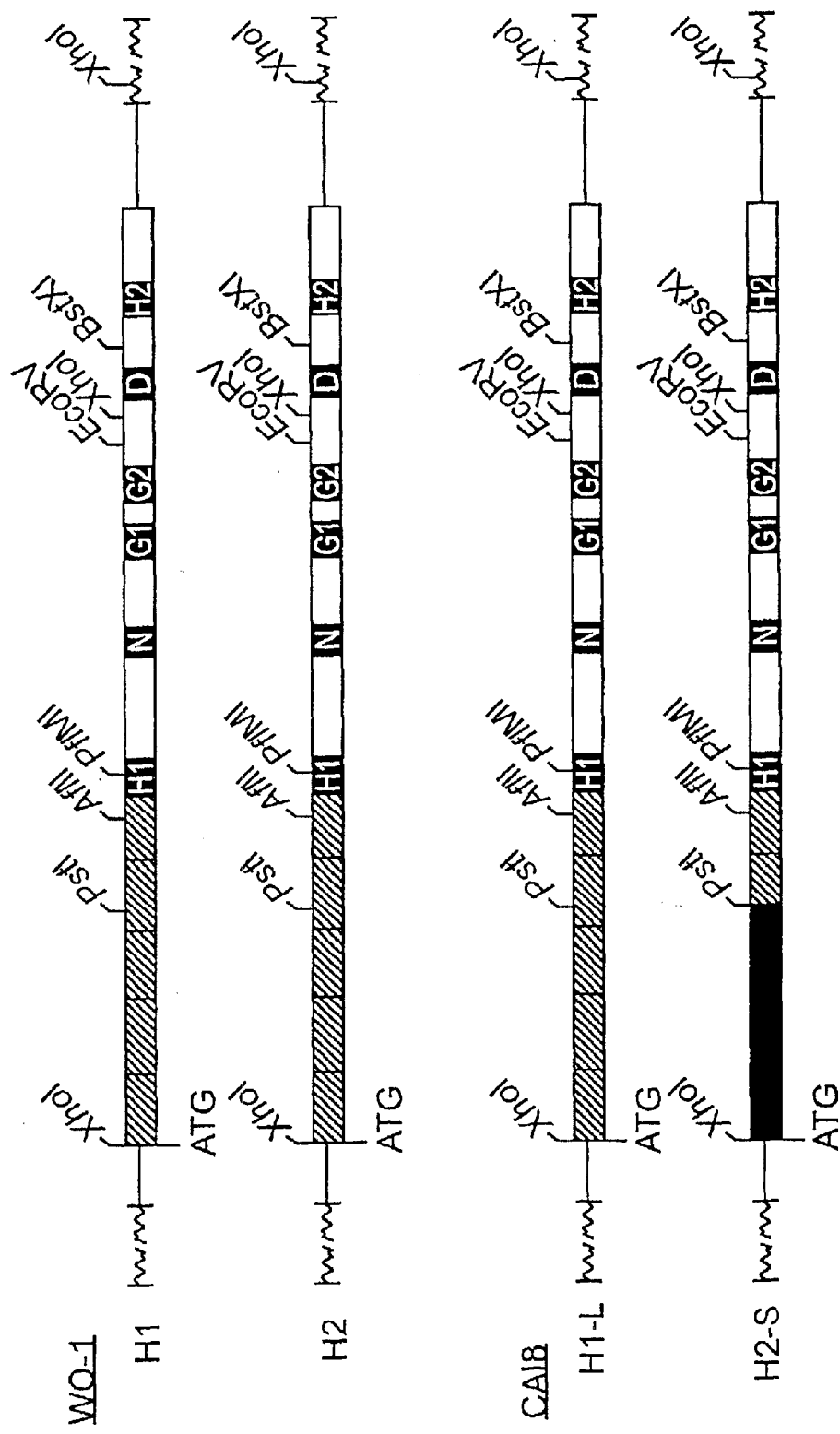
FIG. 3 is a schematic representation of the anatomy of two alleles in two strains of C. albicans according to the present invention. All the functional domains are shown as white bold letters inside each rectangle. A few of the unique restriction enzyme sites are shown at the top of the rectangle. The start of the protein coding region is shown as ATG. WO-1 and CAI8 are the two strains analyzed in this invention. H1 and H2 are two identical alleles of the strain WO-1. H1-L and H2-S represent large and small alleles respectively in strain CAI8. The five hatched rectangular units in each allele represent repeat units described in this invention. The gray rectangular area encompassing XhoI-PstI in H2-S represents the region containing a deletion of approximately one repeat unit length.

Table 1 summarizes the effects of the CaNik1 deletion in HH80 on growth in a variety of solution and conditions, high frequency phenotypic switching, and dimorphism.

DETAILED DESCRIPTION OF PREFERRED EMBODIMENTS

*Candida albicans* is capable of differentiating in a reversible fashion between a bud and a hyphal growth form. Each strain of *C. albicans* can also undergo high frequency phenotypic switching between a limited number of general phenotypes that differ in a variety of traits including putative virulence factors. The frequencies of both of these developmental programs are influenced by environmental conditions. For example, pH and temperature influence the transition between bud and hypha while temperature, UV, white blood cell metabolites and colony aging affect the frequency of high frequency phenotypic switching. The morphological changes made by *C. albicans* in response to environmental cues indicates that the organism uses a sensory mechanism to register and assess environmental alterations.

Autophosphorylating histidine kinases, also known as "two-component response regulators," have been found, in lower eukayotes such as fungi and slime molds, to play a pivotal role in relaying various environmental signals into the cell for inducing appropriate responses and in providing these organisms with the capacity to respond rapidly to an environmental perturbation. Two-component signal transducers all contain a sensory kinase, which autophosphorylates a histidine residue in response to an environmental cue, and a response regulator, which then is phosphorylated and, through a resultant conformational change, effects a signal that is transduced either directly to a molecular complex, as in the case of the bacterial CheY and the flagellar motor, or down a signal transduction pathway, as in the case of SLN1. These proteins have been shown to be involved in regulating morphogenesis and development in various prokaryotes and eukaryotes.

That two-component response regulators have been identified in other yeast species suggests that the two-component response regulators may also play a role in the developmental programs of *C. albicans*. The present invention relates to such a two-component response regulator, the hybrid kinase CaNIK1 from *Candida albicans*. A link between the gene encoding CaNik1 and the processes of phenotypic switching that includes the differential expression of pathogenic genes is evidenced by work with a CaNik1-deletion strain of *C. albicans*. See examples 3 and 5. Thus, CaNik1 is know to be involved in phenotypic switching.

Phenotypic switching is thought to be linked to the virulent characteristics of yeast. *Candida albicans* switches phenotypes with regard to its environment in order to maximize pathogenesis according to the demands of the particular environment. For example, in the WO-1 strain of *Candida albicans*, studies have shown that the yeast is more virulent in its opaque phenotype when located on the skin. When WO-1 is in the white phenotype, however, it is more pathogenic in systemic infections. A description of the relationship between the phenotypic switching and the pathogenic characteristics of *Candida albicans* can be found in Soll, "Switching and Gene Regulation in *Candida albicans*," in SOCIETY FOR GENERAL MICROBIOLOGY SYMPOSIUM 50 (1992). This relationship between phenotypic switching and pathogenicity can be exploited effectively, in a bioassay, for the purpose of discovering pharmaceutical candidates against *Candida albicans*.

1. Definitions

In this description, "isolated DNA" is a fragment of DNA that is not integrated in the genomic DNA of an organism. For example, the CaNik1 gene is a DNA fragment that has been isolated from the genomic DNA of *C. albicans*.

As used herein, "protein" refers to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as PROTEINS—STRUCTURE AND MOLECULAR PROPERTIES (2d ed.), T. E. Creighton, W. H. Freeman and Company, New York (1993).

As used herein, "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The terms "stringent conditions" or stringent hybridization conditions includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Specificity is typically the function of post-hybridization washes, the critical factors being the ionic strength and temperature of the final wash solution. For DNA-DNA hybrids, the $T_m$ can be approximated from the equation of Meinkoth & Wahl, Anal. Biochem. 138: 267–84 (1984): $T_m=81.5°$ C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. But severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, Part I, Chapter 2 "Overview of principles of hybridization and the strategy of nucleic acid probe assays," Elsevier, New York (1993); and in Chapter 2 of CURRENT PROTOCOLS IN MOLECULAR BIOLOGY, Greene Publishing and Wiley-Interscience, New York (1995) (hereafter "Ausubel et al.").

Two nucleic acid molecules are considered to have a "substantial sequence similarity" if their nucleotide sequences share a similarity of at least 50%. Sequence similarity determinations can be performed, for example, using the FASTA program (Genetics Computer Group; Madison, Wis.). Alternatively, sequence similarity determinations can be performed using BLASTP (Basic Local Alignment Search Tool) of the Experimental GENIFO(R) BLAST Network Service. See Altschul et al., "Sequence Similarity Searches, Multiple Sequence Alignments, and Molecular Tree Building," in METHODS IN PLANT MOLECULAR BIOLOGY AND BIOTECHNOLOGY, Glick et al. (eds.), pages 251–267 (CRC Press, 1993).

As used herein "promoter" includes reference to a region of DNA upstream from the start of transcription and involved in recognition and binding of RNA polymerase and other proteins to initiate transcription. Tissue-specific, tissue-preferred, cell type-specific, and inducible promoters constitute the class of "non-constitutive" promoters. A "constitutive" promoter is one that is active under most environmental conditions.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "expression" refers to the biosynthesis of a gene product. For example, in the case of a structural gene, expression involves transcription of the structural gene into mRNA and the translation of mRNA into one or more polypeptides.

As used herein, "expression vector" is a polynucleotide molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked" to the regulatory elements.

2. Isolating a *Candida albicans* Polynucleotide Segment Encoding CaNik1 Protein An endogenous polynucleotide sequence from *Candida albicans* which encodes for the CaNIK1 protein was isolated using a polynucleotide probe derived from PCR amplification. See Example 1. Hybridization of the probe against a genomic library resulted in the determination of the full length polynucleotide sequence encoding the CaNIK1 protein. See Example 2. The full polynucleotide sequence encapsulating the CaNik1 gene is provided in FIG. 2.

3. Nucleic Acids

The present invention provides, inter alia, isolated nucleic acids of RNA, DNA, and analogs and/or chimeras thereof, comprising a polynucleotide encoding a CaNik1 protein or a polynucleotide probe which hybridizes to a polynucleotide encoding CaNIK1 protein. In this regard, the invention provides the nucleotide sequences of FIGS. 1 and 2. In addition, the present invention also provides other sequences as described below.

a. Polynucleotides Encoding A CaNIK1 Polypeptide or Conservatively Modified or Polymorphic Variants Thereof As indicated above, the present invention provides isolated heterologous nucleic acids comprising a polynucleotide, wherein the polynucleotide encodes a CaNIK1 protein, disclosed herein in FIG. 2, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides that are silent variations of the polynucleotides of FIG. 2. The present invention further provides isolated nucleic acids comprising polynucleotides encoding conservatively modified variants of CaNIK1 encoded by the sequences in FIG. 2. Conservatively modified variants can be used to generate or select antibodies immunoreactive to the non-variant polypeptide. Additionally, the present invention further provides isolated nucleic acids comprising polynucleotides encoding one or more polymorphic (allelic) variants of polypeptides/polynucleotides.

b. Polynucleotides That Selectively Hybridize

The present invention also provides isolated nucleic acids comprising polynucleotides, wherein the polynucleotides selectively hybridize, under selective hybridization conditions, to a polynucleotide as discussed above. In this regard, the present invention encompasses polynucleotides that selectively hybridize, under selective conditions, to a polynucleotide as discussed above, excluding the polynucleotide of FIG. 2. Thus, the polynucleotides of this embodiment can be used for isolating, detecting, and/or quantifying nucleic acids comprising the polynucleotides described above. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a nucleic acid library. Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

c. Polynucleotides Having at Least 60% Sequence Identity

The present invention further provides isolated nucleic acids comprising polynucleotides, wherein the polynucleotides have a specified identity at the nucleotide level to a polynucleotide as disclosed above. In this regard, the present invention encompasses polynucleotides that have a specified identity to the polynucleotides discussed above, but are not the same as the sequence of FIG. 2. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

4. Vectors

According to the present invention, the polynucleotide sequence encoding the CaNIK1 protein may be inserted into any suitable yeast vector with any method known to a person who has skill in the art. The vector will typically be comprised of a polynucleotide encoding the CaNIK1 protein operably linked to any suitable promoter which will direct the transcription of the polynucleotide in the intended host cell. Examples of suitable promoters include EF1α2 which is a constitutive promoter and is characterized in Sundstrom et al., *General Bacteriology*, 172: 2036–2045 (1990), and PCK1 which is an inducible promoter and is characterized in Leuker et al., *Gene* 192: 235–240 (1997). According to the present invention, the promoter is operably linked to the polynucleotide encoding for the CaNIK1 protein and inserted into a yeast transformation vector.

Yeast vectors are grouped into five general classes according to their mode of replication in the yeast: YIp, YRp, YCp, YEp, YLp. Comprehensive laboratory techniques regarding insertion of polynucleotides into yeast vectors can be found in Chapter 13 of Ausubel et al.

5. Bioassay

Another aspect of the invention is a bioassay useful for screening pharmaceutical candidates which can inhibit pathogenicity in *Candida albicans*. The bioassay is based on assessing a candidate's ability to inhibit expression or functionality of the CaNik1 gene or its gene product, which as explained above, is linked to the virulent characteristics of the yeast. A bioassay according to the present invention comprises the following steps: transformation of cells from yeast species that exhibit phenotypic switching with a polynucleotide encoding CaNIK1 protein, and a promoter linked to the polynucleotide segment which can drive protein expression; effecting contact between the yeast cells and a pharmaceutical candidate; and analyzing the effect of the pharmaceutical candidate on inhibition of the expression of the CaNik1 gene. In one embodiment, *C. albicans* cells harboring a CaNik1 deletion are transformed with a suitable construct containing a CaNIK1-encoding polynucleotide, and an operably linked promoter.

A. Transformation of Yeast Cells

The present invention contemplates the use of yeast cells with a phenotypic switching pathway similar to that of *Candida albicans*. Srikantha et al., J. Bacteriol. 179: 3837–3844 (1997). Transformation of the cells can be accomplished through any means known to a person with skill in the art. One example of a yeast transformation procedure is the lithium acetate procedure whereby yeast cells are briefly incubated in buffered lithium acetate and transforming DNA is introduced with carrier DNA. Addition of polyethylene glycol (PEG) and a heat shock trigger DNA uptake. An alternate method of transforming yeast cells is the electroporation procedure whereby concentrated cells are transformed using an exponential electric pulse. Comprehensive laboratory techniques regarding yeast transformation procedures can be found in Chapter 13 of Ausubel et al.

B. Contact of a Test Substance with Transformed Cells

According to the present invention, a test substance should make contact with at least some of a plurality of cells transformed with a polypeptide encoding CaNik1. Contact includes any exposure of the test substance to any surface of a transformed cell. A preferred method of contact would be incubation of the cells with the test substance.

The test substance includes any compound which may have characteristics inhibitory to the growth or the pathogenicity of *Candida albicans*. An example of a test substance is a pharmaceutical compound with antimycotic properties.

6. Assessing of the Effect of the Test Substance on CaNik1 Gene Expression

According to the present invention, the effect of the pharmaceutical compound on CaNik1 expression is analyzed after contact between the pharmaceutical compound and the plurality of transformed cells. CaNik1 expression can be measured through any means known by a person with skill in the art. Examples of methods which monitor the level of gene expression are: measuring levels of CaNIK1 protein and mRNA produced by the cells; or measuring the kinase activity within the cell; or monitoring the level of transcription of a reporter gene operably linked to a promoter.

An example of monitoring CaNik1 expression is the measurement of levels of CaNIK1 protein produced by the plurality of cells. This can be measured by performing two-dimensional gel electrophoresis using the techniques of isoelectric-focusing and SDS-polyacrylamide gel electrophoresis followed by autoradiography of the gel. Comprehensive laboratory techniques regarding two-dimensional gel electrophoresis and autoradiography can be found in Chapter 10 and Appendix 3 of Ausubel et al.

Another example of monitoring CaNik1 expression is to measure the level of mRNA encoded within the cell and produced by the plurality. mRNA levels within the cell can be measured with the following three techniques: Northern Blot, primer extension and ribonuclease protection. The Northern Blot procedure consists of fractioning mRNA with gel electrophoresis, transferring the mRNA fragments from the gel onto a filter and hybridizing the target mRNA molecules used a labeled DNA or RNA probe. The primer extension procedure includes hybridizing an oligonucleotide primer to the 5' end of the target mRNA and extending the primer using reverse transcriptase and unlabeled deoxynucleotides to form a single-stranded DNA complementary to the template RNA. The resultant DNA is analyzed on the sequencing gel. The yield of the primer extension product quantifies the amount of mRNA produced by the cell. The ribonuclease protection assay measures mRNA levels by hybridizing sequence specific RNA probes to sample RNAs. The probe anneals to homologous sequences in the sample RNA. The presence of target RNA is analyzed and quantified by gel electrophoresis. Comprehensive laboratory techniques regarding Northern Blot, primer extension and ribonuclease protection assays can be found in Chapter 4 of Ausubel et al.

A third example of monitoring CaNik1 expression is to monitor the level of kinase activity within the plurality of cells. Kinase activity within the cells can be monitored by labeling ATP with $^{32}p$ in vitro. The labeled ATP acts as the donor substrate, and the CaNIK1 protein acts as the acceptor substrate. Phosphotransfer is detected as the accumulation of $^{32}P$-labeled protein within the cell. The accumulation of protein is measured with polyacrylamide gel electrophoresis and autoradiography. Target kinase activity can be distinguished from background kinase activity with autophosphorylation of the CaNIK1 protein on polyacrylamide gel. Comprehensive laboratory techniques regarding phosphorylation and measurement of kinase activity can be found in Chapter 18 of Ausubel et al.

In a further example, a reporter gene is operably linked to a promoter and the level of transcription of the reporter gene is monitored after contact between the plurality and the test substance. In accordance with the present invention, the promoter region of the CaNik1 gene is operably linked to the luciferase gene. Gene activity is thus linked to luciferase activity, which can then be measured quantitively, with a luminometer, as a bioluminescent reaction.

The present invention is described further below by reference to the following examples, which are illustrative only.

EXAMPLE 1
PCR Amplification to Determine a CaNik1 Probe

The following, deoxyinosine-containing, degenerate primers were designed that encompassed the highly conserved regions of the two component response regulators LemA (Hrabak & Willis, *J Bacteriol* 174: 3011–3020 (1992)), BarA (Nagasawa et al., *Escherichia coli. Mol Microbiol*, 6: 799–807 (1992)) and SLN1 (Ota & Varshavasky, *Science* 263: 566–569 (1993)), respectively: 1) Slb1: (SEQ ID NO:5) 5-GAATTGAGAACGCCTITIAATGG-3, which corresponds to the histidine-autokinase domain; 2) Slb2: (SEQ ID NO:6) 5-AGTCCTAAGCCA GTACCACC-3, which corresponds to the ATP-binding domain; and 3) Slb3: (SEQ ID NO:7) 5-TTTAGGCATCTGGACITCCAT, which corresponds to the response regulator domain. Slb1 served as a 5'-end primer for PCR amplifications. The Slb1/Slb2 and Slb1/Slb3 pairs were used to amplify PCR products using the Hot-start wax gem (Perkin, Elmer) protocol. The Hot-start wax gem protocol which generates PCR products used the following reaction mixture: 10 mM Tris-HCl, pH 8.0, 50 mM KCl, 1.2 mM $MgCl_2$, 100 $\mu$M dNTP, 50 $\mu$m of each primer and 2.5 units of Taq polymerase, in a final volume of 100 $\mu$L. Conditions for PCR cycling included denaturation at 94° C. for 1 min, annealing at 40° C. for 1.5 min and extension at 72° C. for 2.5 min. For all amplifications, *S. cerevisiae* genomic DNA was used as a control for the amplification of the two component hybrid kinase gene SLN1, to monitor the quality of the PCR products. PCR products were gel purified and cloned into either PCR-Trap (Hunter Gen) or pGEM T-Easy (Promega Corp.). Three positive clones were chosen for each of the PCR products of the two sets of primer pairs. pCN.5/3, pCN.5/11 and pCN.5/21 were chosen from the products of Slb1/Slb2; and pCN1.3/5, pCN1.3/13 and pCN 1.3/16 were chosen from the products of Slb1/Slb3.

EXAMPLE 2
Isolation of CaNik1 Gene

To isolate a full-length gene, approximately $8 \times 10^4$ plaques of a *C. albicans* genomic library were screened using a 1.2 kb DNA fragment isolated from pCN1.3/13, which spanned the histidine-autokinase (H1) and aspartyl receiver domain (D1). Lambda DNA from 20 positive clones was extracted and Southern blots probed with pCN1.3/13. Using combinations of primer pairs for the arms of the lambda DNA and either the degenerate primers for the histidine-autokinase domain (Slb1) or the response regulator domain (Slb3), lambda clones containing inserts larger than 4 kb were identified. The screen was performed with a high fidelity long PCR protocol (Boehringer Mannheim, Inc., Indianapolis, Ind.). Three lambda clones contained DNA fragments larger than 3 kb that flanked the upstream region of the histidine-autokinase domain and the downstream region of the aspartyl receiver domain. One of these clones, SA15.1, was chosen to determine the complete nucleotide sequence of the gene in both directions using the ABI automated sequencing system and fluorescent dideoxynucleotides as described earlier.

The DNA fragment generated by Slb1/Slb3 was used as a probe to screen a *C. albicans* EMBL3a lambda genomic library to identify clones containing the full-length gene. Of $10^5$ pfu's, twenty positive clones were identified. Clone $\lambda$SA15.1, which contained a genomic fragment of approximately 4.8 kb with DNA flanking both the H1 and the D domains, was chosen for further characterization. The nucleotide sequence of the DNA insert was determined in both directions. The deduced amino acid sequence revealed an uninterrupted open reading frame of 1081 amino acids beginning with ATG as the initiation codon. The initiation codon was surrounded by an atypical Kozak consensus sequence CTCCA<u>ATG</u>A, with cytosine at the −3 position (Kozak, *Nucleic Acids Res*, 12: 857–871 (1984)). When total genomic DNA of *C. albicans* strain WO-1 was digested with a variety of restriction enzymes, and the resulting Southern blot hybridized under conditions of high stringency (65° C. in Church-Gilbert hybridization buffer) (Church & Gilbert, *Proc Natl Acad. Sci USA* 81: 1991–1995 (1984)) with the 1.2 kb probe spanning the 800 bp upstream of the gene, the banding pattern suggested that CaNIK1 is encoded by a single copy gene. When total genomic DNA of strain WO-1 and strain 3153A was digested with BsaAI or NciI and hybridized with the 4.2 kb probe, the patterns were identical, but when TspI-digested DNA of the two strains were probed, the patterns differed, suggesting allelic differences exist between these strains. A comparison of the CaNik1 sequence published recently by Nagahashi et al., *Candida albicans. Microbology*, 144: 425–432 (1998) for strain IFO1060 and the sequence we obtained for strain WO-1 in the present invention differ at seven nucleotide positions in the open reading frame of 3243 bp.

EXAMPLE 3
Deletion of CaNik1 in *C. albicans* Strain CAI8

Figure 4:
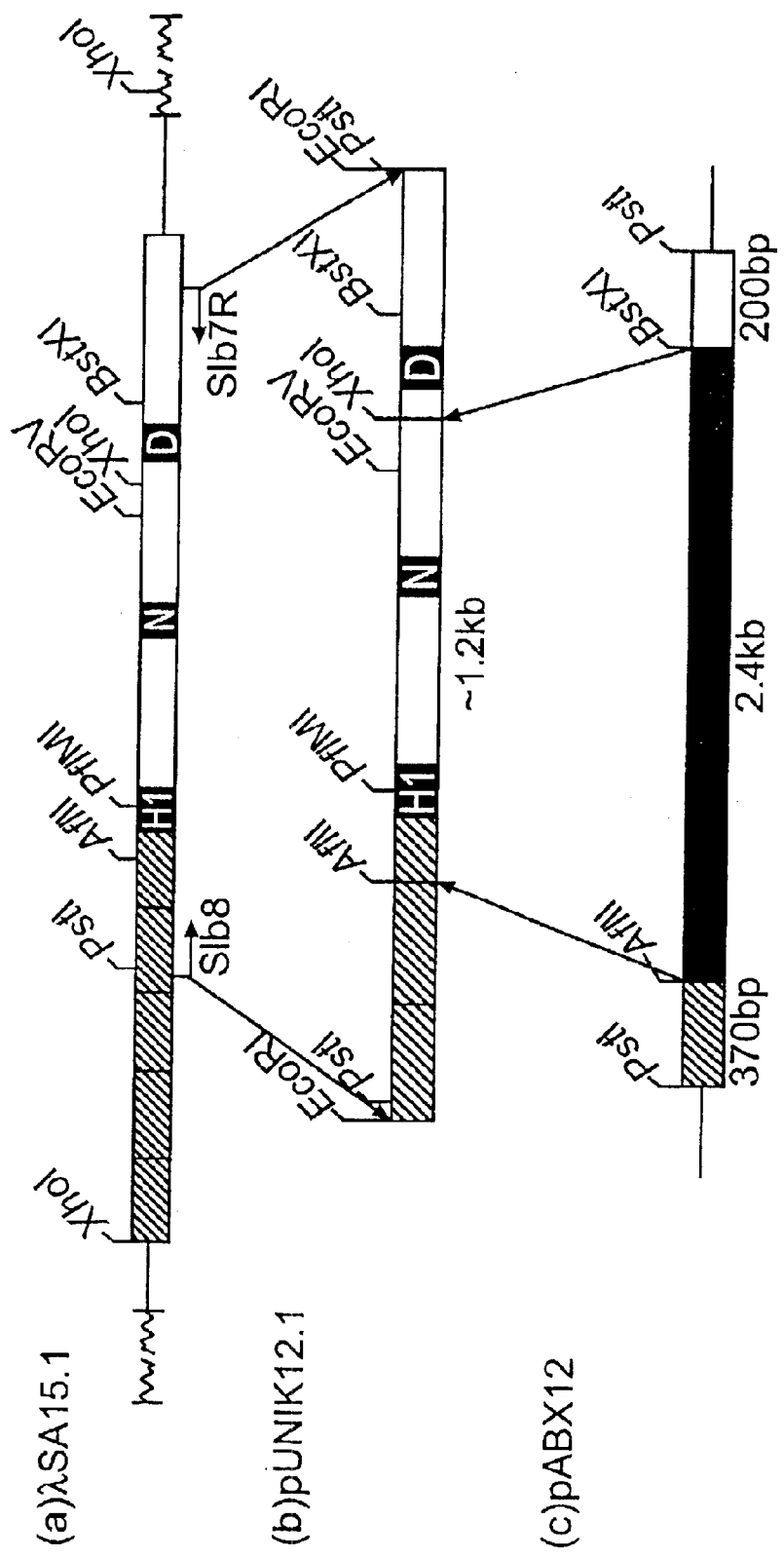
FIG. 4 illustrates the deletion strategy used to generate a homozygous deletion mutant, HH80, in strain CAI8. The region spanning AflII-XhoI was deleted and substituted by a hisG-Urablaster cassette in the plasmid pUNIK12.1 to create pCNH35 (FIG. 4c). Plasmid pUNIK12.1 (FIG. 4b) was derived by subcloning a PCR fragment using a pair of primers Slb8 and Slb7R and subcloning into pGEM-T easy plasmid vector. λSA15.1 represent the lambda clone identified in a screen that contain the genomic fragment encompassing the entire CaNik1 gene and the flanking DNA sequence.

In order to generate a CaNik1 deletion cassette, a DNA fragment of approximately 2.1 kb containing both the histidine-autokinase and aspartyl response regulator domains was amplified by PCR using as the template $\lambda$SA15.1 (FIG. 4a), which contained the 545 bp sequence upstream of the histidine-autokinase domain. The PCR fragment was gel-purified and cloned into the PGEM-T easy vector (Promega). The DNA insert was again excised from the recombinant plasmid with EcoRI and subcloned into a PUC18 vector (Life Technologies) at the EcoRI site. The resultant recombinant plasmid was designated pUNIK12.1 (FIG. 4b). A deletion construct pCNH35 was generated that spanned the histidine-autokinase and ATP binding-domains. To construct pCNH35, pUNIK12.1 plasmid DNA (FIG. 4b) was digested with AflII and XhoI, and blunt-end repaired with the Klenow DNA polymerase I. The resultant plasmid DNA fragment was then gel purified and dephosphorylated with shrimp alkaline phosphatase (US Biochemical). A hisG-URA3-hisG cassette of 3.8 kb from pMB9 was then ligated to derive the disruption cassette (FIG. 4c). To isolate the CaNik1 disruption cassette from pCNH35, plasmid DNA was digested with PstI and the digested DNA extracted with phenol: chloroform. Approximately 25 $\mu$g of the digestion mixture was used to transform strain CAI8, an $ade2^-$ $ura3^-$ derivative of wild type strain SC5314, by the lithium acetate protocol. Heterozygotes were selected for growth in minimal medium in the absence of uridine. Transformants were initially tested for the heterozygosity of one of the two CaNik1 alleles by Southern blot hybridization of genomic DNA digested with PstI. Positive heterozygotes were further confirmed by digesting genomic DNA with XhoI and by performing Southern blot hybridization. Because the genomic Southerns revealed polymorphism between the two CaNik1 alleles, two distinct heterozygotes, NNL6 (L stands for large allele) and NNS7 (S stands for small allele) were selected. The heterozygote NNS7 was chosen to generate the knock-out for the second copy of the CaNIK1 gene. Prior to the knock-out of the second copy, NNS7 was subjected to the 5-FOA selection protocol to convert it from uridine prototrophy to auxotrophy. Loss of the URA3 gene was again confirmed by digestion with XhoI and Southern blot analysis. In the final step, a single clone, NNS7.1.1, which was heterozygous for the L allele of the CaNik1 locus and $URA3^+$, was subjected to a second round of transformation with pCNH35, and selected for growth on defined minimal medium lacking uridine. Transformants which had lost the second copy of CaNik1 were selected by Southern blot hybridization. One of the 125 transformants obtained with the pCNH35-based cassette, HH80, contained a homozygous deletion.

EXAMPLE 4
CaNik1 Transcription

Figure 5:
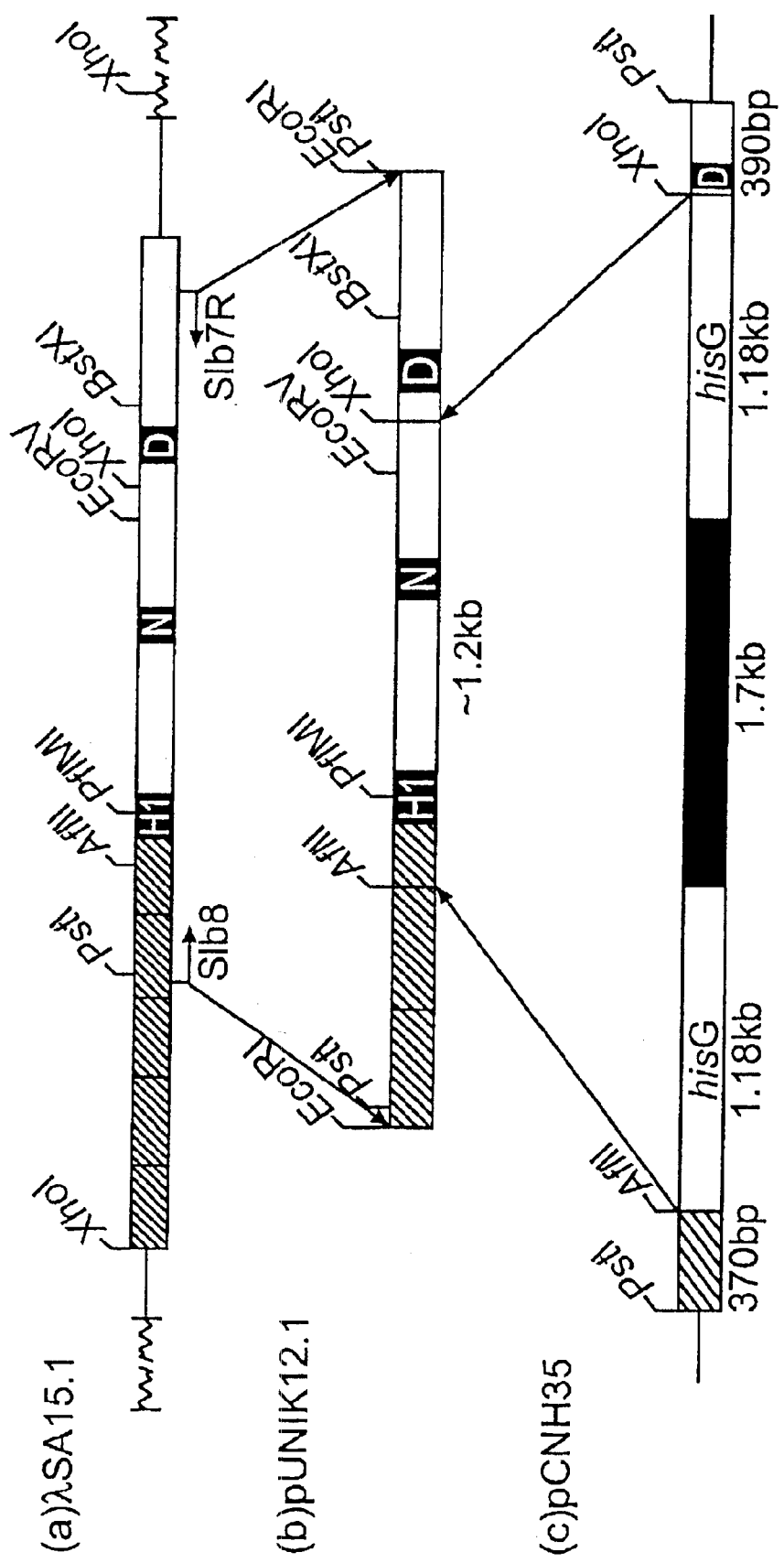
FIG. 5 shows the deletion strategy used to generate the homozygous deletion mutant in Red 3/6, an ade2⁻ derivative of strain WO-1. The deletion cassette pABX12 (FIG. 5b) was generated by deletion of all the functional domains except H2 and substitution with the ADE2 gene as an auxotrophic marker in pUNIK12.1 (FIG. 5c).

To test whether transcription of CaNik1 was regulated by high frequency phenotypic switching, Northern blots of polyA$^+$mRNA of white and opaque phase cell growth cultures of strain WO-1 were probed with the DNA fragment spanning the H1 and ATP binding domains of CaNik1. The CaNik1 transcript was detectable at very low levels in both white phase and opaque phase cells throughout the exponential phase of growth and in stationary phase. The level of CaNik1 transcript per cell remained constant throughout white phase cell growth, but increased steadily during opaque phase cell growth, reaching a level per cell roughly twice that of white phase cells at stationary phase (FIG. 5). Hypha-forming cells of both C. albicans strain WO-1 and C. albicans strain 3153A contained slightly higher levels of polyA$^+$ CaNik1 transcript than budding cells. The hypha-to-bud ratio of polyA$^+$-containing CaNik1 transcript in strain WO-1 and strain 3153A was 1.2 and 1.3, respectively.

EXAMPLE 5
Functional Characterization of the CaNik1 Null Mutant of Strain CAI8

To test whether the CaNik1 deletion mutant HH80 underwent switching, we first had to characterize switching in this strain using a low dose ultraviolet irradiation protocol that increases switching frequencies. Cells were treated with ultraviolet irradiation for 0, 5, 10, 20 and 40 sec, and the percent kill as well as the frequency and type of switch variants were assessed on modified Lee's medium. The proportions of CAI8 and HH80 cells killed after 5, 10, 20, and 40 sec were similar. Identical variant phenotypes were stimulated by UV in both CAI8 and the homozygous deletion strain HH80. However, the frequency of variants induced by comparable levels of UV-irradiation was consistently lower in strain HH80, and this was true in a repeat experiment. For instance, 20 sec of UV irradiation resulted in 10.6% and 2.6% variants in CAI8 and HH80 cells, respectively. These results demonstrate that the CaNik1 gene product modulates phenotypic switching.

Since deletion of the nik-1$^+$ gene in N. crassa affects the morphology of hyphae, especially at high osmotic strength (Alex et al., Proc Natl Acad Sci USA, 93: 3416–3421 (1996), the capability of the CaNik1-minus HH80 strain to form hyphae and the morphology of those hyphae were compared to that of the parent strain CAI8 and a URA3$^+$ isogenic strain CAI8U5 at 0, 1.0 and 1.5 M NaCl. Under the regime of pH-regulated dimorphism, CAI8, CAI8U5, and HH80 cells formed buds at pH 4.5 and hyphae at pH 6.7. The kinetics of evagination for the three strains at low and high pH were similar at the three tested salt concentrations. At 1.5 M NaCl, the proportion of cells that formed evaginations at low and high pH was dramatically reduced in all three strains. The morphology of the hyphae that formed at pH 6.7 at 0, 1.0, and 1.5 M NaCl were comparable in the three strains. However, there was a significant and reproducible lag in hyphal growth at 1.5M NaCl in HH80 after 300 min. These results demonstrate that the CaNik1 gene product is not essential for hypha formation under the regime of pH regulated dimorphism, but its presence enhances hypha formation at high ionic strength.

Finally, growth of the CaNik1 deletion mutant HH80 was tested at 25° C. and 37° C. for differential sensitivity to osmotic strength and a variety of inhibitors. Patches of budding cells of CAI8, CAI8U5 and HH80 were plated on agar containing modified Lee's medium alone or with one of the following ingredients: 1.0 or 1.5M NaCl; 1M sorbitol; 0.8M KCl; 0.5M Mg$_2$SO$_4$; 20 or 40 µg per ml calcofluor; 1, 2 or 4 mg per ml caffeine; 10 or 20 mg per ml hygromycin; 0.002 or 0.004 µg per ml echinocandin; and 0.2 or 0.4M polymyxin B. In three independent experiments, no qualitative differences were observed between the growth of the control strains and the mutant strain HH80 for any of the tested conditions.

All publications and patent applications referred to in this specification are indicative of the level of skill of those in the art to which the invention pertains.

Other objects, features and advantages of the present invention will become apparent from the foregoing detailed description and examples. It should be understood, however, that the detailed description and the specific examples, while indicating preferred embodiments of the invention, are given only by way of illustration.

TABLE 1

| Conditions used to test the effect of gene deletion | *Phenotypic effect in HH80 |
|---|---|
| 1. Growth kinetics in | |
| a) Lee's modified broth | Similar to SC5314, CAI8U5, and CAI8 |
| b) YPD broth | Similar to SC5314, CAI8U5, and CAI8[20]. |
| 2. Growth on agar plates with Lee's modified medium or YPD broth supplemented with: | |
| a) None | ++++ |
| b) 1 M NaCl | ++ |
| c) 1.5 M NaCl | + |
| d) 1 M KCl | ++ |
| e) 1.2 M Sorbitol | ++++ |
| f) 0.5 m MgSO$_4$ | ++ |
| g) Caffeine (1–4 mg/mL) | v |
| h) Calcofluor (20–40 µg/mL) | +++[v] |
| i) Echinocandin (0.002–0.004 µg/mL) | ± |
| j) 2% Trehalose | ++++* |
| k) 2% Raffinose | ++++* |
| l) 1 M Xylitol | ++++ |
| m) 10% Glycerol | ++++* |
| 3. Switching | |
| a) spontaneous frequency | No effect |

TABLE 1-continued

| Conditions used to test the effect of gene deletion | *Phenotypic effect in HH80 |
|---|---|
| b) UV-stimulated frequency | Decreased |
| c) repertoire of switch phenoype | No effect |
| 4. Hypha-induction under the regime of pH-regulated dimorphism. with no osmotic shock: | |
| a) time for 50% evagination | No effect |
| b) morphology of hypha | No effect |
| c) growth of hyphal filaments | |
| with osmotic shock using 1.5 M NaCl | |
| i) time for 50% evaginations | decreased in both wild type and the mutant |
| ii) morphology of hyphac | no difference between wild hyphae and the mutant |
| iii) growth of hyphal filaments | the growth of the hyphae after 300 min was reduced in the mutant as compared to that in wild type |

In order to asses the effect of gene deletion on growth, exponentially grown cells of wild type (SC53 14), parental auxotrophic strain used to delete NIK1 gene (CAI8), URA3+ derivative of CAI8 (CAI8U5) and homozygous deletion mutant (HH80) were serially diluted and spot plated on agar plates with or without supplements in the medium. In all the growth medium used in this study, 2% glucose served as a carbon source except in the growth medium containing raffinose, trehalose and glycerol. The symbol "v" denote variable growth. Growth of the cultures were qualitatively assessed as very good (++++), good (+++), fair (++), poor (+), poor to no growth (±). 0 indicates that colonies were very small (less than 1mm) as assessed by the colony size on agar plates spread with cultures to generate 50 to 100 individual colonies. The growth of the cultures were assessed after 2 or 3 days incubation both at 25° C. and 37° C.

What is claimed is:

1. An isolated polynucleotide that encodes a protein linked to phenotypic switching in *Candida albicans that exhibits* 70% or greater overall sequence identity to SEQ. ID No. 3, wherein said protein displays kinase activity.

2. The polynucleotide of claim 1 that exhibits 80% or greater identity to SEQ ID No 3.

3. The polynucleotide of claim 1 that exhibits 90% or greater identity to SEQ ID NO 3.

4. A polynucleotide according to claim 1, comprising the sequence of SEQ ID No. 3.

5. A method of screening for a compound with the ability to inhibit expression or functionality of the CaNIK1 protein comprising:

(A) contacting a yeast cell that exhibits phenotypic switching with a test substance, wherein said yeast cell comprises:
   (i) a polynucleotide according to claim 1 and
   (ii) a promoter operably linked to said polynucleotide, such that said yeast cell produces a protein encoded by said polynucleotide; then (B) monitoring the ability of said test substance to inhibit expression or functionality of said protein encoded by said polynucleotide in said yeast cell.

6. The method according to claim 5, wherein step (B) comprises monitoring the level of said protein produced in said cell.

7. The method according to claim 6, wherein step (B) comprises effecting a two-dimensional gel electrophoresis.

8. The method according to claim 5, wherein step (B) comprises monitoring the level of m RNA encoded by said polynucleotide and produced by sais cell.

9. The method according to claim 8, wherein step (B) comprises effecting a Northern blot, a primer extension, or a ribonuclease protection assay.

10. The method according to claim 5, wherein step (B) comprises monitoring the level of kinase activity within said yeast cell, wherein said kinase activity typifies said protein.

11. The method according to claim 10, wherein step (B) comprises:

(A) labeling ATP with $^{32}$P in vitro;

(B) running cellular proteins on a polyacrylamide gel; and (C) determining the amount of $^{32}$P labeled protein using autoradiography.

12. The method according to claim 5, wherein a promoter is operably linked to a reporter gene and wherein step (B) comprises monitoring the level of transcription of said reporter gene within said yeast cell.

13. The method according to claim 12, wherein said reporter gene is a luciferase gene and luciferase activity is monitored using a luminometer.

14. An isolated polynuoleotide encoding the amino acid sequence of SEQ ID. NO. 4.

15. A culture of a bacterial strain containing the lambda phage λSG15.1.

* * * * *

SEQUENCE LISTING

<160> NUMBER OF SEQ ID NOS: 7

<210> SEQ ID NO 1
<211> LENGTH: 1254
<212> TYPE: DNA
<213> ORGANISM: Candida albicans
<220> FEATURE:
<221> NAME/KEY: CDS
<222> LOCATION: (1)..(1254)

<400> SEQUENCE: 1

```
gag att aga aca cca ttg aat ggg att att ggw atg acy cag ttg tcr    48
Glu Ile Arg Thr Pro Leu Asn Gly Ile Ile Gly Met Thr Gln Leu Ser
 1               5                  10                  15 ctt gat aca gag ttg acr cag tac caa cga gag atg ttg tcg att gtg    96
Leu Asp Thr Glu Leu Thr Gln Tyr Gln Arg Glu Met Leu Ser Ile Val
             20                  25                  30 cat aac ttg gca aat tcc ttg ttg acc att ata gac gat ata ttg gat   144
His Asn Leu Ala Asn Ser Leu Leu Thr Ile Ile Asp Asp Ile Leu Asp
         35                  40                  45 att tct aag att gag gcg aat aga atg acg gtg gaa cag att gat ttt   192
Ile Ser Lys Ile Glu Ala Asn Arg Met Thr Val Glu Gln Ile Asp Phe
     50                  55                  60 tca tta aga ggg aca gtg ttt ggt gca ttg aaa acg tta gcc gtc aaa   240
Ser Leu Arg Gly Thr Val Phe Gly Ala Leu Lys Thr Leu Ala Val Lys
 65                  70                  75                  80 gct att gaa aaa aac cta gac ttg acc tat caa tgt gat tca tcg ttt   288
Ala Ile Glu Lys Asn Leu Asp Leu Thr Tyr Gln Cys Asp Ser Ser Phe
                 85                  90                  95 cca gat aat ctt att gga gat agt ttt aga tta cga caa gtt att ctt   336
Pro Asp Asn Leu Ile Gly Asp Ser Phe Arg Leu Arg Gln Val Ile Leu
            100                 105                 110
```

| | | |
|---|---|---|
| aac ttg gct ggt aat gct att aag ttt act aaa gag ggg aaa gtt agt<br>Asn Leu Ala Gly Asn Ala Ile Lys Phe Thr Lys Glu Gly Lys Val Ser<br>115                     120                   125 | 384 |
| gtt agt gtg aaa aag tct gat aaa atg gtg tta gat agt aag ttg ttg<br>Val Ser Val Lys Lys Ser Asp Lys Met Val Leu Asp Ser Lys Leu Leu<br>130                     135                   140 | 432 |
| tta gag gtt tgt gtt agc gac acg gga ata ggt ata gag aaa gac aaa<br>Leu Glu Val Cys Val Ser Asp Thr Gly Ile Gly Ile Glu Lys Asp Lys<br>145                     150                   155                   160 | 480 |
| ttg gga ttg att ttc gat acc ttc tgt caa gct gat ggt tct act aca<br>Leu Gly Leu Ile Phe Asp Thr Phe Cys Gln Ala Asp Gly Ser Thr Thr<br>                   165                   170                   175 | 528 |
| aga aag ttt ggt ggt aca ggt tta ggg ttg tca att tcc aaa cag ttg<br>Arg Lys Phe Gly Gly Thr Gly Leu Gly Leu Ser Ile Ser Lys Gln Leu<br>                   180                   185                   190 | 576 |
| ata cat tta atg ggt gga gag ata tgg gtt act tcg gag tat gga tcc<br>Ile His Leu Met Gly Gly Glu Ile Trp Val Thr Ser Glu Tyr Gly Ser<br>                   195                   200                   205 | 624 |
| ggr tca aac ttt tat ttt acg gtg tgc gtg tcg cca tct aat att aga<br>Gly Ser Asn Phe Tyr Phe Thr Val Cys Val Ser Pro Ser Asn Ile Arg<br>210                   215                   220 | 672 |
| tat act cga caa acc gaa caa ttg tta cca ttt agt tcc cat tat gtg<br>Tyr Thr Arg Gln Thr Glu Gln Leu Leu Pro Phe Ser Ser His Tyr Val<br>225                   230                   235                   240 | 720 |
| tta ttt gta tcg act gag cat act caa gaa gaa ctt gat gtg ttg aga<br>Leu Phe Val Ser Thr Glu His Thr Gln Glu Glu Leu Asp Val Leu Arg<br>                   245                   250                   255 | 768 |
| gat gga att ata gaa ctt gga ttg ata cct ata ata gtg aga aat att<br>Asp Gly Ile Ile Glu Leu Gly Leu Ile Pro Ile Ile Val Arg Asn Ile<br>                   260                   265                   270 | 816 |
| gaa gat gca aca ttg act gag ccg gtg aaa tat gat ata att atg att<br>Glu Asp Ala Thr Leu Thr Glu Pro Val Lys Tyr Asp Ile Ile Met Ile<br>                   275                   280                   285 | 864 |
| gat tcg ata gag att gcc aaa aag ttg agg ttg tta tcg gag gtt aaa<br>Asp Ser Ile Glu Ile Ala Lys Lys Leu Arg Leu Leu Ser Glu Val Lys<br>                   290                   295                   300 | 912 |
| tat att ccg ttg gtt ttg gtc cat cat tct att cca cag ttg aat atg<br>Tyr Ile Pro Leu Val Leu Val His His Ser Ile Pro Gln Leu Asn Met<br>305                   310                   315                   320 | 960 |
| aga gta tgt att gat ttg ggg ata tct tcc tat gca aat acg cca tgt<br>Arg Val Cys Ile Asp Leu Gly Ile Ser Ser Tyr Ala Asn Thr Pro Cys<br>                   325                   330                   335 | 1008 |
| tcg atc acg gac ttg gcc agt gcg att ata cca gcg ttg gag tcg aga<br>Ser Ile Thr Asp Leu Ala Ser Ala Ile Ile Pro Ala Leu Glu Ser Arg<br>                   340                   345                   350 | 1056 |
| tct ata tca cag aac tca gac gag tcg gtg agg tac aaa ata tta cta<br>Ser Ile Ser Gln Asn Ser Asp Glu Ser Val Arg Tyr Lys Ile Leu Leu<br>                   355                   360                   365 | 1104 |
| gca gag gac aac ctc gtc aat cag aaa ctt gca gtt agg ata tta gaa<br>Ala Glu Asp Asn Leu Val Asn Gln Lys Leu Ala Val Arg Ile Leu Glu<br>370                   375                   380 | 1152 |
| aag caa ggg cat ctg gtg gaa gta gtt gag aac gga ctc gag gcg tac<br>Lys Gln Gly His Leu Val Glu Val Val Glu Asn Gly Leu Glu Ala Tyr<br>385                   390                   395                   400 | 1200 |
| gaa gcg att aag agg aat aaa tat gat gtg gtg ttg atg gat gtg caa<br>Glu Ala Ile Lys Arg Asn Lys Tyr Asp Val Val Leu Met Asp Val Gln<br>                   405                   410                   415 | 1248 |
| atg cct<br>Met Pro | 1254 |

-continued

```
<210> SEQ ID NO 2
<211> LENGTH: 418
<212> TYPE: PRT
<213> ORGANISM: Candida albicans

<400> SEQUENCE: 2

Glu Ile Arg Thr Pro Leu Asn Gly Ile Ile Gly Met Thr Gln Leu Ser
 1               5                  10                  15

Leu Asp Thr Glu Leu Thr Gln Tyr Gln Arg Glu Met Leu Ser Ile Val
            20                  25                  30

His Asn Leu Ala Asn Ser Leu Leu Thr Ile Ile Asp Asp Ile Leu Asp
        35                  40                  45

Ile Ser Lys Ile Glu Ala Asn Arg Met Thr Val Glu Gln Ile Asp Phe
    50                  55                  60

Ser Leu Arg Gly Thr Val Phe Gly Ala Leu Lys Thr Leu Ala Val Lys
65                  70                  75                  80

Ala Ile Glu Lys Asn Leu Asp Leu Thr Tyr Gln Cys Asp Ser Ser Phe
                85                  90                  95

Pro Asp Asn Leu Ile Gly Asp Ser Phe Arg Leu Arg Gln Val Ile Leu
            100                 105                 110

Asn Leu Ala Gly Asn Ala Ile Lys Phe Thr Lys Glu Gly Lys Val Ser
        115                 120                 125

Val Ser Val Lys Lys Ser Asp Lys Met Val Leu Asp Ser Lys Leu Leu
    130                 135                 140

Leu Glu Val Cys Val Ser Asp Thr Gly Ile Gly Ile Glu Lys Asp Lys
145                 150                 155                 160

Leu Gly Leu Ile Phe Asp Thr Phe Cys Gln Ala Asp Gly Ser Thr Thr
                165                 170                 175

Arg Lys Phe Gly Gly Thr Gly Leu Gly Leu Ser Ile Ser Lys Gln Leu
            180                 185                 190

Ile His Leu Met Gly Gly Glu Ile Trp Val Thr Ser Glu Tyr Gly Ser
        195                 200                 205

Gly Ser Asn Phe Tyr Phe Thr Val Cys Val Ser Pro Ser Asn Ile Arg
    210                 215                 220

Tyr Thr Arg Gln Thr Glu Gln Leu Leu Pro Phe Ser Ser His Tyr Val
225                 230                 235                 240

Leu Phe Val Ser Thr Glu His Thr Gln Glu Glu Leu Asp Val Leu Arg
                245                 250                 255

Asp Gly Ile Ile Glu Leu Gly Leu Ile Pro Ile Val Arg Asn Ile
            260                 265                 270

Glu Asp Ala Thr Leu Thr Glu Pro Val Lys Tyr Asp Ile Ile Met Ile
        275                 280                 285

Asp Ser Ile Glu Ile Ala Lys Lys Leu Arg Leu Leu Ser Glu Val Lys
    290                 295                 300

Tyr Ile Pro Leu Val Leu Val His His Ser Ile Pro Gln Leu Asn Met
305                 310                 315                 320

Arg Val Cys Ile Asp Leu Gly Ile Ser Ser Tyr Ala Asn Thr Pro Cys
                325                 330                 335

Ser Ile Thr Asp Leu Ala Ser Ala Ile Ile Pro Ala Leu Glu Ser Arg
            340                 345                 350

Ser Ile Ser Gln Asn Ser Asp Glu Ser Val Arg Tyr Lys Ile Leu Leu
        355                 360                 365

Ala Glu Asp Asn Leu Val Asn Gln Lys Leu Ala Val Arg Ile Leu Glu
    370                 375                 380
```

```
Lys Gln Gly His Leu Val Glu Val Val Glu Asn Gly Leu Glu Ala Tyr
385                 390                 395                 400

Glu Ala Ile Lys Arg Asn Lys Tyr Asp Val Val Leu Met Asp Val Gln
                405                 410                 415

Met Pro

<210> SEQ ID NO 3
<211> LENGTH: 3246
<212> TYPE: DNA
<213> ORGANISM: Candida albicans
<220> FEATURE:
<221> NAME/KEY: CDS
<222> LOCATION: (1)..(3243)

<400> SEQUENCE: 3 atg aac ccc act aaa aaa cct cgg tta tca cca atg cag ccc tct gtt        48
Met Asn Pro Thr Lys Lys Pro Arg Leu Ser Pro Met Gln Pro Ser Val
 1               5                  10                  15 ttt gaa ata ctc aac gac cct gag ctt tat agt cag cac tgt cat agc        96
Phe Glu Ile Leu Asn Asp Pro Glu Leu Tyr Ser Gln His Cys His Ser
                20                  25                  30 ctt agg gaa aca ctt ctt gat cat ttc aac cat caa gct aca ctt atc       144
Leu Arg Glu Thr Leu Leu Asp His Phe Asn His Gln Ala Thr Leu Ile
            35                  40                  45 gac act tat gaa cat gaa cta gaa aaa tcc aaa aat gcc aac aaa gcg       192
Asp Thr Tyr Glu His Glu Leu Glu Lys Ser Lys Asn Ala Asn Lys Ala
        50                  55                  60 tcc caa caa gca ctt agt gaa ata ggt aca gtt gtt ata tct gtt gcc       240
Ser Gln Gln Ala Leu Ser Glu Ile Gly Thr Val Val Ile Ser Val Ala
 65                  70                  75                  80 atg gga gac ttg tcg aaa aaa gtt gag att cac aca gta gaa aat gac       288
Met Gly Asp Leu Ser Lys Lys Val Glu Ile His Thr Val Glu Asn Asp
                85                  90                  95 cct gag att tta aaa gtc aaa atc acc atc aac acc atg atg gat caa       336
Pro Glu Ile Leu Lys Val Lys Ile Thr Ile Asn Thr Met Met Asp Gln
            100                 105                 110 tta cag aca ttt gct aat gag gtt aca aaa gtc gcc acc gaa gtc gca       384
Leu Gln Thr Phe Ala Asn Glu Val Thr Lys Val Ala Thr Glu Val Ala
        115                 120                 125 aat ggt gaa cta ggt gga caa gcg aaa aat gat gga tct gtt ggt att       432
Asn Gly Glu Leu Gly Gly Gln Ala Lys Asn Asp Gly Ser Val Gly Ile
130                 135                 140 tgg aga tca ctt aca gac aat gtt aat att atg gct ctt aat tta act       480
Trp Arg Ser Leu Thr Asp Asn Val Asn Ile Met Ala Leu Asn Leu Thr
145                 150                 155                 160 aac caa gtg cga gaa att gct gat gtc aca cgt gct gtt gcc aag ggg       528
Asn Gln Val Arg Glu Ile Ala Asp Val Thr Arg Ala Val Ala Lys Gly
                165                 170                 175 gac ttg tca cgt aaa att aat gta cac gcc cag ggt gaa atc ctt caa       576
Asp Leu Ser Arg Lys Ile Asn Val His Ala Gln Gly Glu Ile Leu Gln
            180                 185                 190 ctt caa cgt aca ata aac acc atg gtg gat cag tta cga acg ttt gca       624
Leu Gln Arg Thr Ile Asn Thr Met Val Asp Gln Leu Arg Thr Phe Ala
        195                 200                 205 ttc gaa gta tct aaa gtt gct aga gat gtt ggt gtg ctt ggt ata tta       672
Phe Glu Val Ser Lys Val Ala Arg Asp Val Gly Val Leu Gly Ile Leu
    210                 215                 220 gga gga caa gcg ttg att gaa aat gtt gaa ggt att tgg gaa gag ttg       720
Gly Gly Gln Ala Leu Ile Glu Asn Val Glu Gly Ile Trp Glu Glu Leu
225                 230                 235                 240
```

-continued

```
act gat aat gtc aat gcc atg gct ctt aat ttg act aca caa gtg aga      768
Thr Asp Asn Val Asn Ala Met Ala Leu Asn Leu Thr Thr Gln Val Arg
            245                 250                 255 aat att gcc aat gtc acc act gcc gtt gcc aag ggg gat ttg tcg aaa      816
Asn Ile Ala Asn Val Thr Thr Ala Val Ala Lys Gly Asp Leu Ser Lys
        260                 265                 270 aaa gtc act gct gat tgt aag gga gaa aty ctt gat ttg aaa ctt act      864
Lys Val Thr Ala Asp Cys Lys Gly Glu Ile Leu Asp Leu Lys Leu Thr
            275                 280                 285 att aat caa atg gtg gac cga tta cag aat ttt gct ctt gcg gtg acg      912
Ile Asn Gln Met Val Asp Arg Leu Gln Asn Phe Ala Leu Ala Val Thr
290                 295                 300 aca ttg tcg aga gag gtt ggt act ttg ggt att ttg ggt gga caa gct      960
Thr Leu Ser Arg Glu Val Gly Thr Leu Gly Ile Leu Gly Gly Gln Ala
305                 310                 315                 320 aac gta cag gat gtt gaa ggt gct tgg aaa cag gtt aca gaa aat gtc     1008
Asn Val Gln Asp Val Glu Gly Ala Trp Lys Gln Val Thr Glu Asn Val
                325                 330                 335 aac cta atg gct act aat tta act aac caa gtg aga tct att gct aca     1056
Asn Leu Met Ala Thr Asn Leu Thr Asn Gln Val Arg Ser Ile Ala Thr
            340                 345                 350 gtt act act gca gtt gcg cat ggt gat ttg tcg caa aag att gat ggt     1104
Val Thr Thr Ala Val Ala His Gly Asp Leu Ser Gln Lys Ile Asp Gly
        355                 360                 365 cat ccc aaa gga gag att tta caa ttg aaa aat aca atc aac aag atg     1152
His Pro Lys Gly Glu Ile Leu Gln Leu Lys Asn Thr Ile Asn Lys Met
    370                 375                 380 gtg gac tct ttg cag ttg ttt gca tca gaa gtg tcg aaa gtg gca caa     1200
Val Asp Ser Leu Gln Leu Phe Ala Ser Glu Val Ser Lys Val Ala Gln
385                 390                 395                 400 gat gtt ggt att aat gga aaa tta ggt att caa gca caa gtt agt gat     1248
Asp Val Gly Ile Asn Gly Lys Leu Gly Ile Gln Ala Gln Val Ser Asp
                405                 410                 415 gtt gat gga tta tgg aag gag att acg tct aat gta aat acc atg gct     1296
Val Asp Gly Leu Trp Lys Glu Ile Thr Ser Asn Val Asn Thr Met Ala
            420                 425                 430 tca aat tta act tcg caa gtg aga gct ttt gca cag att act gct gct     1344
Ser Asn Leu Thr Ser Gln Val Arg Ala Phe Ala Gln Ile Thr Ala Ala
        435                 440                 445 gct act gat ggg gat ttc act aga ttt att act gtt gaa gca ctg gga     1392
Ala Thr Asp Gly Asp Phe Thr Arg Phe Ile Thr Val Glu Ala Leu Gly
    450                 455                 460 gag atg gat gcg ttg aaa aca aag att aat caa atg gtg ttt aac tta     1440
Glu Met Asp Ala Leu Lys Thr Lys Ile Asn Gln Met Val Phe Asn Leu
465                 470                 475                 480 agg gaa tcg ctt caa agg aat act gcg gct aga gaa gct gct gag ttg     1488
Arg Glu Ser Leu Gln Arg Asn Thr Ala Ala Arg Glu Ala Ala Glu Leu
                485                 490                 495 gcc aat agt gcg aaa tcc gag ttt tta gca aac atg tcg cat gag att     1536
Ala Asn Ser Ala Lys Ser Glu Phe Leu Ala Asn Met Ser His Glu Ile
            500                 505                 510 aga aca cca ttg aat ggg att att ggw atg acy cag ttg tcr ctt gat     1584
Arg Thr Pro Leu Asn Gly Ile Ile Gly Met Thr Gln Leu Ser Leu Asp
        515                 520                 525 aca gag ttg acr cag tac caa cga gag atg ttg tcg att gtg cat aac     1632
Thr Glu Leu Thr Gln Tyr Gln Arg Glu Met Leu Ser Ile Val His Asn
    530                 535                 540 ttg gca aat tcc ttg ttg acc att ata gac gat ata ttg gat att tct     1680
Leu Ala Asn Ser Leu Leu Thr Ile Ile Asp Asp Ile Leu Asp Ile Ser
```

|  |  |  |  |  |  |  |  |  |  |  |  |  |  |  |  |  |
|---|---|---|---|---|---|---|---|---|---|---|---|---|---|---|---|---|
| 545 |  |  |  | 550 |  |  |  | 555 |  |  |  | 560 |  |  |  |  |
| aag | att | gag | gcg | aat | aga | atg | acg | gtg | gaa | cag | att | gat | ttt | tca | tta | 1728 |
| Lys | Ile | Glu | Ala | Asn | Arg | Met | Thr | Val | Glu | Gln | Ile | Asp | Phe | Ser | Leu |  |
|  |  |  |  |  | 565 |  |  |  | 570 |  |  |  | 575 |  |  |  |
| aga | ggg | aca | gtg | ttt | ggt | gca | ttg | aaa | acg | tta | gcc | gtc | aaa | gct | att | 1776 |
| Arg | Gly | Thr | Val | Phe | Gly | Ala | Leu | Lys | Thr | Leu | Ala | Val | Lys | Ala | Ile |  |
|  |  |  | 580 |  |  |  |  | 585 |  |  |  |  | 590 |  |  |  |
| gaa | aaa | aac | cta | gac | ttg | acc | tat | caa | tgt | gat | tca | tcg | ttt | cca | gat | 1824 |
| Glu | Lys | Asn | Leu | Asp | Leu | Thr | Tyr | Gln | Cys | Asp | Ser | Ser | Phe | Pro | Asp |  |
|  |  | 595 |  |  |  |  | 600 |  |  |  |  | 605 |  |  |  |  |
| aat | ctt | att | gga | gat | agt | ttt | aga | tta | cga | caa | gtt | att | ctt | aac | ttg | 1872 |
| Asn | Leu | Ile | Gly | Asp | Ser | Phe | Arg | Leu | Arg | Gln | Val | Ile | Leu | Asn | Leu |  |
| 610 |  |  |  |  | 615 |  |  |  |  | 620 |  |  |  |  |  |  |
| gct | ggt | aat | gct | att | aag | ttt | act | aaa | gag | ggg | aaa | gtt | agt | gtt | agt | 1920 |
| Ala | Gly | Asn | Ala | Ile | Lys | Phe | Thr | Lys | Glu | Gly | Lys | Val | Ser | Val | Ser |  |
| 625 |  |  |  |  | 630 |  |  |  |  | 635 |  |  |  |  | 640 |  |
| gtg | aaa | aag | tct | gat | aaa | atg | gtg | tta | gat | agt | aag | ttg | ttg | tta | gag | 1968 |
| Val | Lys | Lys | Ser | Asp | Lys | Met | Val | Leu | Asp | Ser | Lys | Leu | Leu | Leu | Glu |  |
|  |  |  |  | 645 |  |  |  |  | 650 |  |  |  |  | 655 |  |  |
| gtt | tgt | gtt | agc | gac | acg | gga | ata | ggt | ata | gag | aaa | gac | aaa | ttg | gga | 2016 |
| Val | Cys | Val | Ser | Asp | Thr | Gly | Ile | Gly | Ile | Glu | Lys | Asp | Lys | Leu | Gly |  |
|  |  |  | 660 |  |  |  |  | 665 |  |  |  |  | 670 |  |  |  |
| ttg | att | ttc | gat | acc | ttc | tgt | caa | gct | gat | ggt | tct | act | aca | aga | aag | 2064 |
| Leu | Ile | Phe | Asp | Thr | Phe | Cys | Gln | Ala | Asp | Gly | Ser | Thr | Thr | Arg | Lys |  |
|  |  | 675 |  |  |  |  | 680 |  |  |  |  | 685 |  |  |  |  |
| ttt | ggt | ggt | aca | ggt | tta | ggg | ttg | tca | att | tcc | aaa | cag | ttg | ata | cat | 2112 |
| Phe | Gly | Gly | Thr | Gly | Leu | Gly | Leu | Ser | Ile | Ser | Lys | Gln | Leu | Ile | His |  |
| 690 |  |  |  |  | 695 |  |  |  |  | 700 |  |  |  |  |  |  |
| tta | atg | ggt | gga | gag | ata | tgg | gtt | act | tcg | gag | tat | gga | tcc | ggr | tca | 2160 |
| Leu | Met | Gly | Gly | Glu | Ile | Trp | Val | Thr | Ser | Glu | Tyr | Gly | Ser | Gly | Ser |  |
| 705 |  |  |  |  | 710 |  |  |  |  | 715 |  |  |  |  | 720 |  |
| aac | ttt | tat | ttt | acg | gtg | tgc | gtg | tcg | cca | tct | aat | att | aga | tat | act | 2208 |
| Asn | Phe | Tyr | Phe | Thr | Val | Cys | Val | Ser | Pro | Ser | Asn | Ile | Arg | Tyr | Thr |  |
|  |  |  |  | 725 |  |  |  |  | 730 |  |  |  |  | 735 |  |  |
| cga | caa | acc | gaa | caa | ttg | tta | cca | ttt | agt | tcc | cat | tat | gtg | tta | ttt | 2256 |
| Arg | Gln | Thr | Glu | Gln | Leu | Leu | Pro | Phe | Ser | Ser | His | Tyr | Val | Leu | Phe |  |
|  |  |  | 740 |  |  |  |  | 745 |  |  |  |  | 750 |  |  |  |
| gta | tcg | act | gag | cat | act | caa | gaa | gaa | ctt | gat | gtg | ttg | aga | gat | gga | 2304 |
| Val | Ser | Thr | Glu | His | Thr | Gln | Glu | Glu | Leu | Asp | Val | Leu | Arg | Asp | Gly |  |
|  |  | 755 |  |  |  |  | 760 |  |  |  |  | 765 |  |  |  |  |
| att | ata | gaa | ctt | gga | ttg | ata | cct | ata | ata | gtg | aga | aat | att | gaa | gat | 2352 |
| Ile | Ile | Glu | Leu | Gly | Leu | Ile | Pro | Ile | Ile | Val | Arg | Asn | Ile | Glu | Asp |  |
| 770 |  |  |  |  | 775 |  |  |  |  | 780 |  |  |  |  |  |  |
| gca | aca | ttg | act | gag | ccg | gtg | aaa | tat | gat | ata | att | atg | att | gat | tcg | 2400 |
| Ala | Thr | Leu | Thr | Glu | Pro | Val | Lys | Tyr | Asp | Ile | Ile | Met | Ile | Asp | Ser |  |
| 785 |  |  |  |  | 790 |  |  |  |  | 795 |  |  |  |  | 800 |  |
| ata | gag | att | gcc | aaa | aag | ttg | agg | ttg | tta | tcg | gag | gtt | aaa | tat | att | 2448 |
| Ile | Glu | Ile | Ala | Lys | Lys | Leu | Arg | Leu | Leu | Ser | Glu | Val | Lys | Tyr | Ile |  |
|  |  |  |  | 805 |  |  |  |  | 810 |  |  |  |  | 815 |  |  |
| ccg | ttg | gtt | ttg | gtc | cat | cat | tct | att | cca | cag | ttg | aat | atg | aga | gta | 2496 |
| Pro | Leu | Val | Leu | Val | His | His | Ser | Ile | Pro | Gln | Leu | Asn | Met | Arg | Val |  |
|  |  |  | 820 |  |  |  |  | 825 |  |  |  |  | 830 |  |  |  |
| tgt | att | gat | ttg | ggg | ata | tct | tcc | tat | gca | aat | acg | cca | tgt | tcg | atc | 2544 |
| Cys | Ile | Asp | Leu | Gly | Ile | Ser | Ser | Tyr | Ala | Asn | Thr | Pro | Cys | Ser | Ile |  |
|  |  | 835 |  |  |  |  | 840 |  |  |  |  | 845 |  |  |  |  |
| acg | gac | ttg | gcc | agt | gcg | att | ata | cca | gcg | ttg | gag | tcg | aga | tct | ata | 2592 |
| Thr | Asp | Leu | Ala | Ser | Ala | Ile | Ile | Pro | Ala | Leu | Glu | Ser | Arg | Ser | Ile |  |
| 850 |  |  |  |  | 855 |  |  |  |  | 860 |  |  |  |  |  |  |
| tca | cag | aac | tca | gac | gag | tcg | gtg | agg | tac | aaa | ata | tta | cta | gca | gag | 2640 |

-continued

| | | |
|---|---|---|
| Ser Gln Asn Ser Asp Glu Ser Val Arg Tyr Lys Ile Leu Leu Ala Glu<br>865     870     875     880 | | |
| gac aac ctc gtc aat cag aaa ctt gca gtt agg ata tta gaa aag caa<br>Asp Asn Leu Val Asn Gln Lys Leu Ala Val Arg Ile Leu Glu Lys Gln<br>     885     890     895 | | 2688 |
| ggg cat ctg gtg gaa gta gtt gag aac gga ctc gag gcg tac gaa gcg<br>Gly His Leu Val Glu Val Val Glu Asn Gly Leu Glu Ala Tyr Glu Ala<br>900     905     910 | | 2736 |
| att aag agg aat aaa tat gat gtg gtg ttg atg gat gtg caa atg cct<br>Ile Lys Arg Asn Lys Tyr Asp Val Val Leu Met Asp Val Gln Met Pro<br>   915     920     925 | | 2784 |
| gta atg ggt ggg ttt gaa gct acg gag aag att cga caa tgg gag aaa<br>Val Met Gly Gly Phe Glu Ala Thr Glu Lys Ile Arg Gln Trp Glu Lys<br>930     935     940 | | 2832 |
| aag tct aac cca att gac tcg ttg acc ttt agg act cca att att gcc<br>Lys Ser Asn Pro Ile Asp Ser Leu Thr Phe Arg Thr Pro Ile Ile Ala<br>945     950     955     960 | | 2880 |
| ctc act gca cac gcc atg tta ggt gat aga gaa aag tca ttg gcc aag<br>Leu Thr Ala His Ala Met Leu Gly Asp Arg Glu Lys Ser Leu Ala Lys<br>     965     970     975 | | 2928 |
| ggg atg gac gat tat gtg agt aag cca ttg aag ccg aaa ttg tta atg<br>Gly Met Asp Asp Tyr Val Ser Lys Pro Leu Lys Pro Lys Leu Leu Met<br>980     985     990 | | 2976 |
| cag acg ata aag aag tgt att cat aat att aac cag ttg aaa gaa ttg<br>Gln Thr Ile Lys Lys Cys Ile His Asn Ile Asn Gln Leu Lys Glu Leu<br>   995     1000     1005 | | 3024 |
| tcg aga aat agt agg ggt agc gat ttt gca aag aag atg acc cga aac<br>Ser Arg Asn Ser Arg Gly Ser Asp Phe Ala Lys Lys Met Thr Arg Asn<br>1010     1015     1020 | | 3072 |
| aca ccc ggc cgc acg acc cgt cag ggg agt gat gag ggg agt gta aag<br>Thr Pro Gly Arg Thr Thr Arg Gln Gly Ser Asp Glu Gly Ser Val Lys<br>1025     1030     1035     1040 | | 3120 |
| gac atg att ggg gac act ccc cgt caa ggg agt gtg gag gga ggg ggt<br>Asp Met Ile Gly Asp Thr Pro Arg Gln Gly Ser Val Glu Gly Gly Gly<br>     1045     1050     1055 | | 3168 |
| aca agt agt aga cca gta cag aga agg tct gcc agg gag ggg tcg atc<br>Thr Ser Ser Arg Pro Val Gln Arg Arg Ser Ala Arg Glu Gly Ser Ile<br>     1060     1065     1070 | | 3216 |
| act aca att agt gaa caa atc gac cgt tag<br>Thr Thr Ile Ser Glu Gln Ile Asp Arg<br>   1075     1080 | | 3246 |

<210> SEQ ID NO 4
<211> LENGTH: 1081
<212> TYPE: PRT
<213> ORGANISM: Candida albicans

<400> SEQUENCE: 4

Met Asn Pro Thr Lys Lys Pro Arg Leu Ser Pro Met Gln Pro Ser Val
1     5     10     15

Phe Glu Ile Leu Asn Asp Pro Glu Leu Tyr Ser Gln His Cys His Ser
     20     25     30

Leu Arg Glu Thr Leu Leu Asp His Phe Asn His Gln Ala Thr Leu Ile
   35     40     45

Asp Thr Tyr Glu His Glu Leu Glu Lys Ser Lys Asn Ala Asn Lys Ala
50     55     60

Ser Gln Gln Ala Leu Ser Glu Ile Gly Thr Val Val Ile Ser Val Ala
65     70     75     80

Met Gly Asp Leu Ser Lys Lys Val Glu Ile His Thr Val Glu Asn Asp

-continued

```
                    85                  90                  95
Pro Glu Ile Leu Lys Val Lys Ile Thr Ile Asn Thr Met Met Asp Gln
                100                 105                 110
Leu Gln Thr Phe Ala Asn Glu Val Thr Lys Val Ala Thr Glu Val Ala
            115                 120                 125
Asn Gly Glu Leu Gly Gly Gln Ala Lys Asn Asp Gly Ser Val Gly Ile
        130                 135                 140
Trp Arg Ser Leu Thr Asp Asn Val Asn Ile Met Ala Leu Asn Leu Thr
145                 150                 155                 160
Asn Gln Val Arg Glu Ile Ala Asp Val Thr Arg Ala Val Ala Lys Gly
                165                 170                 175
Asp Leu Ser Arg Lys Ile Asn Val His Ala Gln Gly Glu Ile Leu Gln
                180                 185                 190
Leu Gln Arg Thr Ile Asn Thr Met Val Asp Gln Leu Arg Thr Phe Ala
            195                 200                 205
Phe Glu Val Ser Lys Val Ala Arg Asp Val Gly Val Leu Gly Ile Leu
        210                 215                 220
Gly Gly Gln Ala Leu Ile Glu Asn Val Glu Gly Ile Trp Glu Glu Leu
225                 230                 235                 240
Thr Asp Asn Val Asn Ala Met Ala Leu Asn Leu Thr Thr Gln Val Arg
                245                 250                 255
Asn Ile Ala Asn Val Thr Thr Ala Val Ala Lys Gly Asp Leu Ser Lys
                260                 265                 270
Lys Val Thr Ala Asp Cys Lys Gly Glu Ile Leu Asp Leu Lys Leu Thr
            275                 280                 285
Ile Asn Gln Met Val Asp Arg Leu Gln Asn Phe Ala Leu Ala Val Thr
        290                 295                 300
Thr Leu Ser Arg Glu Val Gly Thr Leu Gly Ile Leu Gly Gly Gln Ala
305                 310                 315                 320
Asn Val Gln Asp Val Glu Gly Ala Trp Lys Gln Val Thr Glu Asn Val
                325                 330                 335
Asn Leu Met Ala Thr Asn Leu Thr Asn Gln Val Arg Ser Ile Ala Thr
            340                 345                 350
Val Thr Thr Ala Val Ala His Gly Asp Leu Ser Gln Lys Ile Asp Gly
        355                 360                 365
His Pro Lys Gly Glu Ile Leu Gln Leu Lys Asn Thr Ile Asn Lys Met
    370                 375                 380
Val Asp Ser Leu Gln Leu Phe Ala Ser Glu Val Ser Lys Val Ala Gln
385                 390                 395                 400
Asp Val Gly Ile Asn Gly Lys Leu Gly Ile Gln Ala Gln Val Ser Asp
                405                 410                 415
Val Asp Gly Leu Trp Lys Glu Ile Thr Ser Asn Val Asn Thr Met Ala
            420                 425                 430
Ser Asn Leu Thr Ser Gln Val Arg Ala Phe Ala Gln Ile Thr Ala Ala
        435                 440                 445
Ala Thr Asp Gly Asp Phe Thr Arg Phe Ile Thr Val Glu Ala Leu Gly
    450                 455                 460
Glu Met Asp Ala Leu Lys Thr Lys Ile Asn Gln Met Val Phe Asn Leu
465                 470                 475                 480
Arg Glu Ser Leu Gln Arg Asn Thr Ala Ala Arg Glu Ala Ala Glu Leu
                485                 490                 495
Ala Asn Ser Ala Lys Ser Glu Phe Leu Ala Asn Met Ser His Glu Ile
                500                 505                 510
```

-continued

```
Arg Thr Pro Leu Asn Gly Ile Ile Gly Met Thr Gln Leu Ser Leu Asp
        515                 520                 525

Thr Glu Leu Thr Gln Tyr Gln Arg Glu Met Leu Ser Ile Val His Asn
    530                 535                 540

Leu Ala Asn Ser Leu Leu Thr Ile Ile Asp Asp Ile Leu Asp Ile Ser
545                 550                 555                 560

Lys Ile Glu Ala Asn Arg Met Thr Val Glu Gln Ile Asp Phe Ser Leu
                565                 570                 575

Arg Gly Thr Val Phe Gly Ala Leu Lys Thr Leu Ala Val Lys Ala Ile
            580                 585                 590

Glu Lys Asn Leu Asp Leu Thr Tyr Gln Cys Asp Ser Ser Phe Pro Asp
        595                 600                 605

Asn Leu Ile Gly Asp Ser Phe Arg Leu Arg Gln Val Ile Leu Asn Leu
    610                 615                 620

Ala Gly Asn Ala Ile Lys Phe Thr Lys Glu Gly Lys Val Ser Val Ser
625                 630                 635                 640

Val Lys Lys Ser Asp Lys Met Val Leu Asp Ser Lys Leu Leu Leu Glu
                645                 650                 655

Val Cys Val Ser Asp Thr Gly Ile Gly Ile Glu Lys Asp Lys Leu Gly
            660                 665                 670

Leu Ile Phe Asp Thr Phe Cys Gln Ala Asp Gly Ser Thr Thr Arg Lys
        675                 680                 685

Phe Gly Gly Thr Gly Leu Gly Leu Ser Ile Ser Lys Gln Leu Ile His
    690                 695                 700

Leu Met Gly Gly Glu Ile Trp Val Thr Ser Glu Tyr Gly Ser Gly Ser
705                 710                 715                 720

Asn Phe Tyr Phe Thr Val Cys Val Ser Pro Ser Asn Ile Arg Tyr Thr
                725                 730                 735

Arg Gln Thr Glu Gln Leu Leu Pro Phe Ser Ser His Tyr Val Leu Phe
            740                 745                 750

Val Ser Thr Glu His Thr Gln Glu Glu Leu Asp Val Leu Arg Asp Gly
        755                 760                 765

Ile Ile Glu Leu Gly Leu Ile Pro Ile Ile Val Arg Asn Ile Glu Asp
    770                 775                 780

Ala Thr Leu Thr Glu Pro Val Lys Tyr Asp Ile Met Ile Asp Ser
785                 790                 795                 800

Ile Glu Ile Ala Lys Lys Leu Arg Leu Leu Ser Glu Val Lys Tyr Ile
                805                 810                 815

Pro Leu Val Leu Val His His Ser Ile Pro Gln Leu Asn Met Arg Val
            820                 825                 830

Cys Ile Asp Leu Gly Ile Ser Ser Tyr Ala Asn Thr Pro Cys Ser Ile
        835                 840                 845

Thr Asp Leu Ala Ser Ala Ile Ile Pro Ala Leu Glu Ser Arg Ser Ile
    850                 855                 860

Ser Gln Asn Ser Asp Glu Ser Val Arg Tyr Lys Ile Leu Leu Ala Glu
865                 870                 875                 880

Asp Asn Leu Val Asn Gln Lys Leu Ala Val Arg Ile Leu Glu Lys Gln
                885                 890                 895

Gly His Leu Val Glu Val Val Glu Asn Gly Leu Glu Ala Tyr Glu Ala
            900                 905                 910

Ile Lys Arg Asn Lys Tyr Asp Val Val Leu Met Asp Val Gln Met Pro
        915                 920                 925
```

-continued

```
Val Met Gly Gly Phe Glu Ala Thr Glu Lys Ile Arg Gln Trp Glu Lys
    930                 935                 940

Lys Ser Asn Pro Ile Asp Ser Leu Thr Phe Arg Thr Pro Ile Ile Ala
945                 950                 955                 960

Leu Thr Ala His Ala Met Leu Gly Asp Arg Glu Lys Ser Leu Ala Lys
                965                 970                 975

Gly Met Asp Asp Tyr Val Ser Lys Pro Leu Lys Pro Lys Leu Leu Met
            980                 985                 990

Gln Thr Ile Lys Lys Cys Ile His Asn Ile Asn Gln Leu Lys Glu Leu
        995                 1000                1005

Ser Arg Asn Ser Arg Gly Ser Asp Phe Ala Lys Lys Met Thr Arg Asn
    1010                1015                1020

Thr Pro Gly Arg Thr Thr Arg Gln Gly Ser Asp Glu Gly Ser Val Lys
1025                1030                1035                1040

Asp Met Ile Gly Asp Thr Pro Arg Gln Gly Ser Val Glu Gly Gly Gly
                1045                1050                1055

Thr Ser Ser Arg Pro Val Gln Arg Arg Ser Ala Arg Glu Gly Ser Ile
            1060                1065                1070

Thr Thr Ile Ser Glu Gln Ile Asp Arg
        1075                1080

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Degenerate
      primer
<221> NAME/KEY: modified_base
<222> LOCATION: (16)
<223> OTHER INFORMATION: i
<221> NAME/KEY: modified_base
<222> LOCATION: (18)
<223> OTHER INFORMATION: i

<400> SEQUENCE: 5
gaattgagaa cgcctntnaa tgg                                      23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Degenerate
      primer
<221> NAME/KEY: modified_base
<222> LOCATION: (3)
<223> OTHER INFORMATION: i

<400> SEQUENCE: 6
agncctaagc cagtaccacc                                          20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Degenerate
      primer
<221> NAME/KEY: modified_base
<222> LOCATION: (16)
```

-continued

```
<223> OTHER INFORMATION: i

<400> SEQUENCE: 7
tttaggcatc tggacntcca t                                           21
```